United States Patent [19]
Goeddel et al.

[11] Patent Number: 6,060,303
[45] Date of Patent: May 9, 2000

[54] TRAF INHIBITORS

[75] Inventors: David V. Goeddel, Hillsborough; Mike Rothe, San Mateo, both of Calif.

[73] Assignees: Genetech, Inc.; Tularik, Inc., both of South San Francisco, Calif.

[21] Appl. No.: 09/020,467

[22] Filed: Feb. 9, 1998

Related U.S. Application Data

[62] Division of application No. 08/700,749, Aug. 14, 1996, Pat. No. 5,789,550.
[60] Provisional application No. 60/002,382, Aug. 17, 1985.
[51] Int. Cl.[7] .............................. C12N 1/20; C07H 21/04
[52] U.S. Cl. ................................... 435/252.3; 435/320.1; 536/23.1; 536/23.5
[58] Field of Search ............................. 435/252.3, 320.1; 536/23.1, 23.5

[56] References Cited

U.S. PATENT DOCUMENTS 4,861,587  8/1989  Urbaschek et al. .

FOREIGN PATENT DOCUMENTS 417563  3/1991  European Pat. Off. .
418014  3/1991  European Pat. Off. .

OTHER PUBLICATIONS

*EMBL Sequence Database* Accession No. U51907 (Mar. 20, 1996).
*Pharmacia Catalog* pp. 133, 142–143 (1994).
*Clonetech Catalog* pp. 19, 192–194 (1994).
Ausubel et al., "Introduction of DNA Into Mammalian Cells" *Current Protocols in Molecular Biology* 1:9.11–9.1.4 (1990).
Berg, J., "Zinc Fingers and Other Metal–Binding Domains" *Journal of Biological Chemsitry* 265(12):6513–6516 (1990).
Beutler, B. and Cerami, A., "Tumor necrosis, cachexia, shock, and inflammation: a common mediator" *Ann. Rev. Biochem.* 57:505–518 (1988).
Blake et al., "The sequences of the human and mouse c–cbl proto–oncogenes show v–cbl was generated by a large truncation encompassing a proline–rich domain and a leucine zipper–like motif" *Oncogene* 6:653–657 (1991).
Brockhaus et al., "Identification of two types of tumor necrosis factor receptors on human cell lines by monoclonal antibodies" *Proc. Natl. Acad. Sci. USA* 87:3127–3131 (1990).
Chan et al., "Molecular definition and sequence motifs of the 52–kD component of human SS–A/Ro Autoantigen" *J. Clin. Invest.* 87:68–76 (1991).
Cheng and Baltimore, "TANK, a co–inducer with TRAF 2 of TNF–and CD40L–mediated NF–kB activation" *Genes & Development* 10:963–973 (1996).
Cheng et al., "Involvement of CRAF1, a relative of TRAF, in CD40 signaling" *Science* 267(8):1494–1498.

Chevray et al., "Protein interaction cloning in yeast: identification of mammalian proteins that react with the Leucine Zipper of June" *Proc. Natl. Acad. Sci. USA* 89:5789–5793 (1992).
Chien et al., "The Two–Hybrid System: A method to identify and clone genes for proteins that interact with a protein of interest" *Proc. Natl. Acad. Sci. USA* 88:9578–9582 (1991).
Deng et al., "COP1, an arabidopsis regulatory gene, encodes a protein with both a zinc–binding motif and a G, homologous domain" *Cell* 71:791–801 (1992).
Driscoll and Williams, "Two divergently transcribed genes of dictyostelium discoideum are cyclic AMP–inducible and coregulated during development" *Molecular & Cellular Biology* 7(12):4482–4489 (1987).
Engelmane tal., "Antibodies to a Soluble Form of a Tumor Necrosis Factor (TNF) Receptor Have TNF–like Activity" *Journal of Biological Chemistry* 265(24):14497–14504 (1990).
Espevik et al., "Characterization of binding and biological effects of monoclonal antibodies against a human tumor necrosis factor receptor" *Journal of Experimental Medicine* 171:415–426 (1990).
Fields and Song, "A novel genetic system to detect protein–protein interactions" *Nature* 340:245–246 (1989).
Fiers, W., "Tumor necrosis factor characterization at the molecular, cellular and In Vivo level" *FEBS Letters*285(2):199–212 (1991).
Freemont et al., "A novel cysteine–rich sequence motif" *Cell* 64:483–484 (1991).
Genethon, "EMBL Seqeunce Database" *Accession No. Z43715 XP002018922* (Nov. 6, 1994).
Goeddel et al., "Tumor Necrosis Factors: Gene Structure and Biological Activities" *Cold Spring Harbor Symposia on Quantitative Biology* LI:597–609 (1986).
Goodwin et al., "Molecular cloning and expression of the type 1 and type 2 murine receptors for tumor necrosis factor" *Molecular & Cellular Biology* 11:3020–3026 (1991).
Gray et al., "Cloning and Expression of cDNA for Human Lymphotoxin, a Lymphokine with Tumor Necrosis Activity" *Nature* 312:721–724 (1984).
Haupt et al., "Novel zinc finger gene implicated as myc collaborator by retrovirally accelerated lymphomagenesis in E$\mu$–myc transgenic mice" *Cell* 65:753–763 (1991).
Hohmann et al., "Expression of the types A and B tumor necrosis factor (TNF) receptors is independently regulated, and both receptors mediate activation of the transcription factor NF–kB" *Journal of Biological Chemistry* 265:22409–22417 (1990).

*Primary Examiner*—Laurie Scheiner
*Attorney, Agent, or Firm*—Ginger Dreger; Diane L. Marschang

[57] ABSTRACT

The invention concerns novel inhibitors of tumor necrosis factor receptor associated factor-(TRAF) mediated signal transduction. The invention encompasses the novel inhibitor proteins (I-TRAFs), nucleic acid encoding them, methods for their recombinant production, and their use in screening assays and as pharmaceuticals.

12 Claims, 5 Drawing Sheets

Hohmann et al., "Two different cell types have different major receptors for human tumor necrosis factor (TNFα)" *Journal of Biological Chemistry* 264(25):14927–14934 (1989).

Hoog, C. *Nucleic Acids Research* 19:6123–27 (1991).

Hoog, C., "Sequential Listing 1" *EMBL Sequence Database* Accession No. X61807 (Sep. 4, 1991).

Hsu et al., "The TNF receptor 1–associated protein TRADD signals cell death and NF–kB activation" *Cell* 81:495–504 (1995).

Hu et al., "A novel RING finger protein interacts with the cytoplasmic domain of CD40" *Journal of Biological Chemistry* 269(48):30069–30072 (1994).

Inoue et al., "Genomic binding–site cloning reveals an estrogen–responsive gene that encodes a ring finger protein" *Proc. Natl. Acad. Sci. USA* 90:11117–11121 (1993).

Inui et al., "Identification of the intracytoplasmic region essential for signal transduction through a B cell activiation molecule, CD40" *European Journal of Immunology* 20:1747–1753 (1990).

Itoh et al., "Protein heterogeneity in the human Ro/SSA ribonucleoproteins" *J. Clin. Invest.* 8:177–186 (1991).

Jones et al., "The saccharomyces cerevisiae RAD18 gene encodes a protein that contains potential zinc finger domains for nucleic acid binding and a putative nucleotide binding sequence" *Nucl. Acids Res.* 16(14):7119–7131 (1988).

Kohno et al., "A second tumor necrosis factor receptor gene product can shed a naturally occurring tumor necrosis factor inhibitor" *Proc. Natl. Acad. Sci. USA* 87:8331–8335 (1990).

Laegreid et al., "Tumor necrosis factor receptor p75 mediates cell–specific activation of nuclear factor kB and induction of human cytomegalovirus enhancer" *Journal of Biological Chemistry* 269:7785–7791 (1994).

Laherty et al., "The Epstein–Barr virus LMP1 gene product induces A20 zinc finger protein expression by activating nuclear factor kB" *Journal of Biological Chemistry* 267:24157 (1992).

Landschulz et al., "The leucine zipper: a hypothetical structure common to a new class of DNA binding proteins" *Science* 204:1759–1764 (1988).

Lenardo and Baltimore, "NF–kB: A pleitropic mediator of inducilbe and tissue–specific gene control" *Cell* 58:227–229 (1989).

Lewis et al., "Cloning and expressionof cDNAs for two distinct murine tumor necrosis factor receptors demonstrate one receptor is species specific" *Proc. Natl. Acad. Sci. USA* 88:2830–2834 (1991).

Liou and Baltimore, "Regulation of the NF–kB/rel transcription factor and 1kB inhibitor sysstem" *Curr. Opin. Cell Biol.* 5:477–487 (1993).

Loetscher et al., "Molecular Cloning and Expression of the Human 55 kd Tumor Necrosis Factor Receptor" *Cell* 61:351–359 (Apr. 20, 1990).

Mardon and Page, "The sex–determining region of the mouse Y chromosome encodes a protein with a highly acidic domain and 13 zinc fingers" *Cell* 56:765–770 (1989).

Miller et al., "Repetitive zinc–binding domains in the protein transcription factor IIIA from Xenopus Oocytes" *EMBO Journal* 4(6):1609–1614 (1985).

Miyatake et al., "Structure of the chromosomal gene for granulocyte–macrophage colony stimulating factor: comparison of the mouse and human genes" *EMBO Journal* 4:2561–2568 (1985).

Mosialos et al., "The Epstein–Barr virus transforming protein LMP1 engages signaling proteins for the tumor necrosis factor receptor family" *Cell* 80:389–399 (1995).

Naume, B. et al., "Involvement of the 55–and 75–kDa tumor necrosis factor receptors in the generation of lymphokine–activated killer cell activity and proliferation of natural killer cells" *J. Immunol.* 146:3035–3048 (1991).

Neta et al., "Comparison of the In Vivo effects of rIL–1 and rTNF in radioprotection, induction of CSF and of acute phase reactants" *Fed. Proc.* (Abstract) 46(4):1200 (1987).

Neta et al., "Interdependent of the radioprotective effects of human recombinant interleukin 1α, tumor necrosis factor α, granulocyte colony–stimulating factor, and murine recombinant granulocyte–macrophage colony–stimulating factor" *J. Immunol.* 140(1):108–111 (1988).

Neta et al., "Interleukin 1 is a radioprotector" *J. Immunol.* 136(7):2483–2485 (Apr. 1, 1986).

Nietfeld et al., "Second–order repeats in xenopus laevis finger proteins" *J. Mol. Biol.* 208:639–659 (1989).

Nophar et al., "Soluble forms of tumor necrosis factor receptors (TNF–Rs). The cDNA for the type 1 TNF–R, cloned using amino acid sequence data of its soluble form, encodes both the cell surface and a soluble form of the receptor" *EMBO Journal* 9:3269–3278 (1990).

Old, L.J., "Tumor Necrosis Factor" *Sci. Am.* 258(5):59–75 (1988).

Opipari et al., "The A20 cDNA induced by tumor necrosis factor α encodes a Novel type of zinc finger protein" *Journal of Biological Chemistry* 265:14705–14708 (1990).

Patarca et al., "rpt–1, an intracellular protein from helper/imducer T cells that regulates gene expression of interleukin 2 receptor and human immunodeficiency virus type1" *Proc. Natl. Acad. Sci. USA* 85:2733–2737 (1988).

Pennica et al., "Human Tumour Necrosis Factor: Precursor Structure, Expression and Homology to Lymphotoxin" *Nature* 312:724–729 (1984).

Reddy et al., "A novel zinc finger coiled–coil domain in a family of nuclear proteins" *Trends Biochem. Sci.* 17:344–345 (1992).

Rothe et al., "I–TRAF is a novel TRAF–interacting protein that regualtes TRAF–mediated signal transduction [C[C[C" *Proceedings of the National Academy of Sciences* 93(16):8241–8246 (1996).

Rothe et al., "The TNFR2–TRAF signalling complex contains two novel proteins related to baculoviral inhibitor of apoptosis proteins" *Cell* 83(7):1243–1252 (1995).

Rowe et al., "Upregulation of bcl–2 by the Epstein–Barr virus latent membrane protein LMP1: a B–cell–specific response that is delayed relative to NF–kB activation and to induction of cell surface markers" *Journal of Virology* 68:5602 (1994).

Ruiz i Altaba et al., "Xfin: an embryonic gene encoding a multifingered protein in Xenopus" *EMBO Journal* 6(10):3065–3070 (1987).

Sambrook et al., *Molecular Cloning, A Laboratory Manual* Chapter 16:16.3–16.81 (1989).

Schall et al., "Molecular Cloning and Expression of a Receptor for Human Tumor Necrosis Factor" *Cell* 61:361–370 (Apr. 20, 1990).

Schatz et al., "The V(D)J recombination activating gene, RAG–1" *Cell* 59:1035–1048 (1989).

Schindler and Baichwal, "Three NF–kB binding sites in the human E–selectin gene required for maximal tumor necrosis factor alpha–induced expression" *Molecular & Cellular Biology* 14(9):5820–5831 (1994).

Shalaby et al., "Binding and regulation of cellular functions by monoclonal antibodies against human tumor necrosis factor receptors" *Journal of Experimental Medicine* 172:1517–1520 (1990).

Smith and Johnson, "Single–step purification of polypeptide expressed in *Escherichia coli* as fusions with glutathione S–transferase" *Gene* 67:31–40 (1988).

Smith et al., "A Receptor for Tumor Necrosis Factor Defines an Unusual Family of Cellular and Viral Proteins" *Science* 248:1019–1023 (May 25, 1990).

Smith et al., "The TNF receptor superfamily of cellular and viral proteins: activation, costimulation, and death" *Cell* 76:959–962 (1994).

Song et al., "The tumor necrosis factor–inducible zinc finger protein A20 interacts with TRAF1/TRAF2 and inhibits NF–kappaB activation" *Proceedings of the National Academy of Sciences* 93(13):6721–6725 (1996).

Stanley et al., "The structure and expresion of the murine gene encoding granulocyte–macrophage colony stimulating factor: evidence for utilization of alternatives promoters" *EMBO Journal* 4:2569–2573 (1985).

Takahashi et al., "Developmentally regulated expression of a human finger–containing gene encoded by the 5' half of the ret transforming gene" *Molecular & Cellular Biology* 8(4):1853–1856 (1988).

Tartaglia and Goeddel, "Two TNF receptors" *Immunology Today* 13:151–153 (1992).

Tartaglia et al., "Stimulation of human T–cell proliferation by specific activation of the 85–kDa tumor necrosis factor receptor" *Proc. Natl. Acad. Sci. USA* 151:4637–4641 (1993).

Tartaglia et al., "The two different receptors for tumor necrosis factor mediate distinct cellular responses" *Proc. Natl. Acad. Sci. USA* 88:9292–9296 (1991).

Thanos and Maniatis, "NF–kB: A lesson in family values" *Cell* 80:529–532 (1995).

Tomita et al., "The neurospora uvs–2 gene encodes a protein which has homology to yeast RAD18, with unique zinc finger motifs" *Mol. Gen. Genet.* 238:225–233 (1993).

Urbaschek et al., "Tumor necrosis factor induced stimulation of granulopoiesis and radioprotection" *Lymphokine Research* 6(3):179–186 (1987).

Vinson et al., "Scissors–grip model for DNA recognition by a family of leucine zipper proteins" *Science* 246:911–916 (1989).

Wiegmann et al., "Human 55–kDa receptor for tumor necrosis factor coupled to signal transduction cascades" *Journal of Biological Chemistry* 267:17997–18001 (1992).

```
         β                    *                α
mouse    MSLKRHSLRRNACHLETRAGIPTILYSDATGQRGMDKNIGEQLNRAYEAF          50
human                                      MDKNIGEQLNKAYEAF          16 mouse    RQACMDRDSAVRELQQKTENYEQRIREQQEQLSFQQNLIDRLKSQLLLVD         100
human    RQACMDRDSAVKELQQKTENYEQRIREQQEQLSLQQTIIDKLKSQLLLVN          66 mouse    SSRDNSYGMVPLLEDSDRRKNNLTLDEPHDKVKLGTLRDKQSKVRRQEVS         150
human    STQDNNYGCVPLLEDSDIRKNILTLAQPQDKVISGIAREKLPKVRRQEVS         116 mouse    SG-KEHSAKGLNIPLHERLNIEKTWDLKEEFHRICLLAKAQKDHLSKL          198
human    SPRKETSARSLGSPLHERNNIEKTSWDLKEEFHKICMLAKAQKDHLSKL         166

>ERRVCQLETTMCSM
mouse    NIPDIATLTQCSVPIQCTDKTEKQEALFKPQAKDDINRGMSCVTAVTPRG         248
human    NIPDIATETQCSVPIQCTDKTDKQEALFIPQAKDDINRGAPSITSVTPRG         216 mouse    LGRDEEDTSFESLSKFNVKFPPMDNDSIFLHSTPEAPSILAPATHDVCQ         298
human    LDRDEEDTSLESLSKFNVKFPPMDNDSIFLHSTPERPGILSPATSEAVCQ         266 mouse    DRFNMEMRDNPGNFVKTEETLFEIQGIDPIISAIQNLKTTDKTNPSNLRA         348
human    EKFNMEFRDNPGNFVKTEETLFEIQGIDPIASAIQNLKTTDKTKPSNLVN         316 mouse    TC---------LPAGDHNVFYVNIFPLQDPHDAPFPSLDSPGKAMRGPQ         388
human    TCIRTTLDRAACLPHGDHNALYVNGFPLIDPSDAPFPSLDSPGKAIRGPQ         366

>VTVLH
mouse    QPFWKPFLNQDIDLVVHSDSDSELLKPLVCEFCQELFPPSITSRGDFLRH         438
human    QPIWKPFHNQDSDSVVLSGTDSELHIPRVCEFCQAVFPPSITSRGDFLRH         416 mouse    LNIHFNGET                                                  447
human    LNSHFNGET                                                  425
```

FIG. 1a

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 413 amino acids
        (B) TYPE: Amino Acid
        (D) TOPOLOGY: Linear (xi) SEQUENCE DESCRIPTION: SEQ ID NO:1:

-continued

```
Met Asp Lys Asn Ile Gly Glu Gln Leu Asn Arg Ala Tyr Glu Ala
 1               5                  10                  15

Phe Arg Gln Ala Cys Met Asp Arg Asp Ser Ala Val Arg Glu Leu
                20                  25                  30

Gln Gln Lys Thr Glu Asn Tyr Glu Gln Arg Ile Arg Glu Gln Gln
                35                  40                  45

Glu Gln Leu Ser Phe Gln Gln Asn Leu Ile Asp Arg Leu Lys Ser
                50                  55                  60

Gln Leu Leu Leu Val Asp Ser Ser Arg Asp Asn Ser Tyr Gly Tyr
                65                  70                  75

Val Pro Leu Leu Glu Asp Ser Asp Arg Arg Lys Asn Asn Leu Thr
                80                  85                  90

Leu Asp Glu Pro His Asp Lys Val Lys Leu Gly Thr Leu Arg Asp
                95                 100                 105

Lys Gln Ser Lys Val Arg Arg Gln Glu Val Ser Ser Gly Lys Glu
               110                 115                 120

Ser Ala Lys Gly Leu Asn Ile Pro Leu His His Glu Arg Asp Asn
               125                 130                 135

Ile Glu Lys Thr Phe Trp Asp Leu Lys Glu Glu Phe His Arg Ile
               140                 145                 150

Cys Leu Leu Ala Lys Ala Gln Lys Asp His Leu Ser Lys Leu Asn
               155                 160                 165

Ile Pro Asp Ile Ala Thr Asp Thr Gln Cys Ser Val Pro Ile Gln
               170                 175                 180

Cys Thr Asp Lys Thr Glu Lys Gln Glu Ala Leu Phe Lys Pro Gln
               185                 190                 195

Ala Lys Asp Asp Ile Asn Arg Gly Met Ser Cys Val Thr Ala Val
               200                 205                 210

Thr Pro Arg Gly Leu Gly Arg Asp Glu Glu Asp Thr Ser Phe Glu
               215                 220                 225

Ser Leu Ser Lys Phe Asn Val Lys Phe Pro Pro Met Asp Asn Asp
               230                 235                 240

Ser Ile Phe Leu His Ser Thr Pro Glu Ala Pro Ser Ile Leu Ala
               245                 250                 255

Pro Ala Thr Pro Glu Thr Val Cys Gln Asp Arg Phe Asn Met Glu
               260                 265                 270

Val Arg Asp Asn Pro Gly Asn Phe Val Lys Thr Glu Glu Thr Leu
               275                 280                 285

Phe Glu Ile Gln Gly Ile Asp Pro Ile Thr Ser Ala Ile Gln Asn
               290                 295                 300

Leu Lys Thr Thr Asp Lys Thr Asn Pro Ser Asn Leu Arg Ala Thr
               305                 310                 315

Cys Leu Pro Ala Gly Asp His Asn Val Phe Tyr Val Asn Thr Phe
               320                 325                 330

Pro Leu Gln Asp Pro Asp Ala Pro Phe Pro Ser Leu Asp Ser
               335                 340                 345

Pro Gly Lys Ala Val Arg Gly Pro Gln Gln Pro Phe Trp Lys Pro
               350                 355                 360

Phe Leu Asn Gln Asp Thr Asp Leu Val Val Pro Ser Asp Ser Asp
               365                 370                 375

Ser Glu Leu Leu Lys Pro Leu Val Cys Glu Phe Cys Gln Glu Leu
               380                 385                 390

Phe Pro Pro Ser Ile Thr Ser Arg Gly Asp Phe Leu Arg His Leu
```

```
                      395                 400                 405
Asn Thr His Phe Asn Gly Glu Thr
                        410                 413

(2) INFORMATION FOR SEQ ID NO:2:

(i) SEQUENCE CHARACTERISTICS:
        (A) LENGTH: 1955 base pairs
        (B) TYPE: Nucleic Acid
        (C) STRANDEDNESS: Single
        (D) TOPOLOGY: Linear (xi) SEQUENCE DESCRIPTION: SEQ ID NO:2:

CTGGAACGGA AAGCTACTTC CGGTTGCAGT CATTCTGCCG GGCACCGGCG                50

ACCTGTGGCG TGAGCGAGCA CAGCCGGAAC CCTCCACTAG CTGGCATTCC               100

TACCATCCTT TATAGTGATG CTACAGGACA AAGAGGAATG GATAAAAACA               150

TTGGTGAGCA ACTCAATAGA GCATATGAAG CCTTCCGACA GGCATGCATG               200

GATAGAGATT CAGCAGTAAG AGAGCTACAG CAAAAGCAGA CTGAGAACTA               250

TGAACAAAGA ATACGCGAGC AACAGGAACA GCTGTCATTT CAACAAAACC               300

TAATTGACAG GCTGAAATCA CAGCTACTTC TCGTGGATTC TAGTCGAGAT               350

AACAGTTATG GCTATGTACC TTTGCTTGAA GACAGTGACA GAAGGAAGAA               400

TAATTTGACC CTTGATGAAC CACATGATAA AGTGAAACTA GGAACACTGA               450

GAGATAAGCA ATCAAAGGTG AGACGACAAG AAGTTTCTTC TGGAAAAGAA               500

TCCGCCAAGG GTCTCAACAT CCCTCTGCAT CACGAAAGGG ATAATATAGA               550

GAAGACTTTC TGGGACCTTA AGAAGAATT TCATAGGATT TGCTTGCTAG                600

CAAAAGCACA GAAAGATCAC TTAAGCAAAC TTAATATACC AGATATTGCA               650

ACTGACACAC AGTGTTCTGT GCCTATACAG TGTACTGATA AAACAGAGAA               700

ACAAGAAGCG CTGTTTAAGC CCCAGGCTAA AGATGATATA AATAGAGGTA               750

TGTCGTGCGT CACAGCTGTC ACACCAAGAG GACTGGGCCG GGATGAGGAA               800

GATACCTCTT TTGAATCACT TTCTAAATTC AATGTCAAGT TTCCGCCTAT               850

GGACAATGAC TCTATTTTTC TACATAGCAC TCCAGAGGCC CCGAGCATCC               900

TTGCTCCTGC CACACCTGAG ACAGTGTGCC AGGACCGATT TAATATGGAA               950

GTCAGAGACA ACCCAGGAAA CTTTGTTAAA ACAGAAGAAA CTTTATTTGA              1000

AATTCAGGGA ATTGACCCCA TAACTTCAGC TATACAAAAC CTTAAAACAA              1050

CTGACAAAAC AAACCCCTCA AATCTTAGAG CGACGTGTTT GCCAGCTGGA              1100

GACCACAATG TGTTCTATGT AAATACGTTC CCACTTCAAG ACCCGCCTGA              1150

CGCACCTTTT CCCTCACTGG ATTCCCCAGG AAAGGCTGTC CGAGGACCAC              1200

AGCAGCCCTT TTGGAAGCCT TTTCTTAACC AAGACACTGA CTTAGTGGTA              1250

CCAAGTGATT CAGACTCAGA GCTCCTTAAA CCTCTAGTGT GTGAATTCTG              1300

TCAAGAGCTT TTCCCACCAT CCATTACATC CAGAGGGGAT TTCCTCCGGC              1350

ATCTTAATAC ACACTTTAAT GGGGAGACTT AAATCACGTT TGAAAACAGA              1400

CATATCATGT TCTCTGTGGT GGTTTTGGAT TTGTAACGCT AGAGAACGCT              1450

TTCTCGTGAG CCAAATGTAA GATTGATTAT AAAGTTGTTA CTTTATCTTT              1500

TAAGAGATCA TTTTGTATAG AACTATAACT CATTATATTA TTCATGTTTA              1550

TACCTATAAT TTCTACATTT CAAAATTACA CATGTGACTT ACAGAGTTAT              1600
```

```
TCAGTCATAA TTTATGTTTC AAATAGCTAA GTTTATTGTT TGACTATTGT          1650

GAGATCTATT AAATTTAGTA ATAGCAAATG TTTATAGGAT ATTCAAATTT          1700

CATTTGAATT TTTAATTATT TTTGCTACAG GTAATATTCC TTTAAAATAC          1750

GTATATAACG TACAGAGAAT AACAGACAAT ATGATCTAAG TAAATGTCGA          1800

ATCAATCATT AGTTGCCCAG GGAAATTTAA ACATTATAGA TCATTTTTAA          1850

ATAATACACA TAGTTTTAAT TTTTACTGTG TGTATAGATG CATGATTAAA          1900

TGACTTAAAT ATTAAAAGTG ACTTACGTCG TGCTTATTAA AAAAAAAAA           1950

AAAAA                                                           1955

(2) INFORMATION FOR SEQ ID NO:3:

(i) SEQUENCE CHARACTERISTICS:
        (A) LENGTH: 34 amino acids
        (B) TYPE: Amino Acid
        (D) TOPOLOGY: Linear (xi) SEQUENCE DESCRIPTION: SEQ ID NO:3:

Met Ser Leu Lys Arg His Ser Leu Arg Arg Asn Ala Cys His Leu
1               5                   10                  15

Glu Thr Arg Ala Gly Ile Pro Thr Ile Leu Tyr Ser Asp Ala Thr
                20                  25                  30

Gly Gln Arg Gly
            34

(2) INFORMATION FOR SEQ ID NO:4:

(i) SEQUENCE CHARACTERISTICS:
        (A) LENGTH: 170 base pairs
        (B) TYPE: Nucleic Acid
        (C) STRANDEDNESS: Single
        (D) TOPOLOGY: Linear (xi) SEQUENCE DESCRIPTION: SEQ ID NO:4:

CCCACGCGTC CGGTTTGGGC AGCATCTGTA GAGCCTGTGC AAACGGCTTC          50

CAGAATGGGT ACGTGCCTAT GTCTTTAAAG AGACATAGTC TGCGAAGGAA          100

CGCCTGTCAC CTGGAGACGA GAGCTGGCAT TCCTACCATC CTTTATAGTG          150

ATGCTACAGG ACAAAGAGGA                                           170

(2) INFORMATION FOR SEQ ID NO:5:

(i) SEQUENCE CHARACTERISTICS:
        (A) LENGTH: 425 amino acids
        (B) TYPE: Amino Acid
        (D) TOPOLOGY: Linear (xi) SEQUENCE DESCRIPTION: SEQ ID NO:5:

Met Asp Lys Asn Ile Gly Glu Gln Leu Asn Lys Ala Tyr Glu Ala
1               5                   10                  15

Phe Arg Gln Ala Cys Met Asp Arg Asp Ser Ala Val Lys Glu Leu
                20                  25                  30

Gln Gln Lys Thr Glu Asn Tyr Glu Gln Arg Ile Arg Glu Gln Gln
                35                  40                  45

Glu Gln Leu Ser Leu Gln Gln Thr Ile Ile Asp Lys Leu Lys Ser
                50                  55                  60

Gln Leu Leu Leu Val Asn Ser Thr Gln Asp Asn Asn Tyr Gly Cys
                65                  70                  75
```

-continued

```
Val Pro Leu Leu Glu Asp Ser Asp Thr Arg Lys Asn Thr Leu Thr
                80                  85                  90

Leu Ala Gln Pro Gln Asp Lys Val Ile Ser Gly Ile Ala Arg Glu
                95                 100                 105

Lys Leu Pro Lys Val Arg Arg Gln Val Ser Ser Pro Arg Lys
            110                 115                     120

Glu Thr Ser Ala Arg Ser Leu Gly Ser Pro Leu Leu His Glu Arg
            125                 130                     135

Gly Asn Ile Glu Lys Thr Ser Trp Asp Leu Lys Glu Glu Phe His
            140                 145                     150

Lys Ile Cys Met Leu Ala Lys Ala Gln Lys Asp His Leu Ser Lys
            155                 160                     165

Leu Asn Ile Pro Asp Thr Ala Thr Glu Thr Gln Cys Ser Val Pro
            170                 175                     180

Ile Gln Cys Thr Asp Lys Thr Asp Lys Gln Glu Ala Leu Phe Thr
            185                 190                     195

Pro Gln Ala Lys Asp Asp Ile Asn Arg Gly Ala Pro Ser Ile Thr
            200                 205                     210

Ser Val Thr Pro Arg Gly Leu Cys Arg Asp Glu Glu Asp Thr Ser
            215                 220                     225

Leu Glu Ser Leu Ser Lys Phe Asn Val Lys Phe Pro Pro Met Asp
            230                 235                     240

Asn Asp Ser Thr Phe Leu His Ser Thr Pro Glu Arg Pro Gly Ile
            245                 250                     255

Leu Ser Pro Ala Thr Ser Glu Ala Val Cys Gln Glu Lys Phe Asn
            260                 265                     270

Met Glu Phe Arg Asp Asn Pro Gly Asn Phe Val Lys Thr Glu Glu
            275                 280                     285

Thr Leu Phe Glu Ile Gln Gly Ile Asp Pro Ile Ala Ser Ala Ile
            290                 295                     300

Gln Asn Leu Lys Thr Thr Asp Lys Thr Lys Pro Ser Asn Leu Val
            305                 310                     315

Asn Thr Cys Ile Arg Thr Thr Leu Asp Arg Ala Ala Cys Leu Pro
            320                 325                     330

Pro Gly Asp His Asn Ala Leu Tyr Val Asn Ser Phe Pro Leu Leu
            335                 340                     345

Asp Pro Ser Asp Ala Pro Phe Pro Ser Leu Asp Ser Pro Gly Lys
            350                 355                     360

Ala Ile Arg Gly Pro Gln Gln Pro Ile Trp Lys Pro Phe Pro Asn
            365                 370                     375

Gln Asp Ser Asp Ser Val Val Leu Ser Gly Thr Asp Ser Glu Leu
            380                 385                     390

His Ile Pro Arg Val Cys Glu Phe Cys Gln Ala Val Phe Pro Pro
            395                 400                     405

Ser Ile Thr Ser Arg Gly Asp Phe Leu Arg His Leu Asn Ser His
            410                 415                     420

Phe Asn Gly Glu Thr
                425
```

(2) INFORMATION FOR SEQ ID NO:6:

(i) SEQUENCE CHARACTERISTICS:
        (A) LENGTH: 2108 base pairs
        (B) TYPE: Nucleic Acid (C) STRANDEDNESS: Single
(D) TOPOLOGY: Linear (xi) SEQUENCE DESCRIPTION: SEQ ID NO:6:

| | | |
|---|---|---|
| GTTTGAGCAG CATTGTTAGA GCCTGTGGAA AACACTTTAC AACTGTGTAA | 50 |
| CTGTCTTCAT CTTTACAGAG GAATAGTCTA CAAAGGAAGA CTTGTAACCT | 100 |
| GGAGAAGAGA CCTGTCATTT ACTCCATCCT TTATAGTGAT GCTACAGGAC | 150 |
| GAAGAGGAAT GGATAAAAAC ATTGGCGAGC AACTCAATAA AGCGTATGAA | 200 |
| GCCTTCCGGC AGGCATGCAT GGATAGAGAT TCTGCAGTAA AAGAATTACA | 250 |
| GCAAAAGACT GAGAACTATG AGCAGAGAAT ACGTGAACAA CAGGAACAGC | 300 |
| TGTCACTCCA ACAGACTATT ATTGACAAGC TAAAATCTCA GTTACTTCTT | 350 |
| GTGAATTCCA CTCAAGATAA CAATTATGGC TGTGTCCCTC TGCTTGAAGA | 400 |
| CAGTGACACA AGAAAGAATA CTTTGACTCT TGCTCAGCCA CAAGATAAAG | 450 |
| TGATTTCAGG AATAGCAAGA GAAAAACTAC CAAAGGTAAG AAGACAAGAG | 500 |
| GTTTCTTCTC CTAGAAAAGA AACTTCAGCA AGGAGTCTTG GCAGTCCTTT | 550 |
| GCTCCATGAA AGGGGTAATA TAGAGAAGAC TTCCTGGGAT CTGAAAGAAG | 600 |
| AATTTCATAA AATATGCATG CTAGCAAAAG CACAGAAAGA CCACTTAAGC | 650 |
| AAACTTAATA TACCAGACAC TGCAACTGAA ACACAGTGCT CTGTGCCTAT | 700 |
| ACAGTGTACG GATAAAACAG ATAAACAAGA AGCGCTGTTT ACGCCTCAGG | 750 |
| CTAAAGATGA TATAAATAGA GGTGCACCAT CCATCACATC TGTCACACCA | 800 |
| AGAGGACTGT GCAGAGATGA GGAAGACACC TCTTTGGAAT CACTTTCTAA | 850 |
| ATTCAATGTC AAGTTTCCAC CTATGGACAA TGACTCAACT TTCTTACATA | 900 |
| GCACTCCAGA GAGACCCGGC ATCCTTAGTC CTGCCACGTC TGAGGCAGTG | 950 |
| TGCCAAGAGA AATTTAATAT GGAGTTCAGA GACAACCCAG GGAACTTTGT | 1000 |
| TAAAACAGAA GAAACTTTAT TTGAAATTCA GGGAATTGAC CCCATAGCTT | 1050 |
| CAGCTATACA AAACCTTAAA ACAACTGACA AAACAAAGCC CTCAAATCTC | 1100 |
| GTAAACACTT GTATCAGGAC AACTCTGGAT AGAGCTGCGT GTTTGCCACC | 1150 |
| TGGAGACCAT AATGCATTAT ATGTAAATAG CTTCCCACTT CTGGACCCAT | 1200 |
| CTGATGCACC TTTTCCCTCA CTCGATTCCC CGGGAAAAGC AATCCGAGGA | 1250 |
| CCACAGCAGC CCATTTGGAA GCCCTTTCCT AATCAAGACA GTGACTCGGT | 1300 |
| GGTACTAAGT GGCACAGACT CAGAACTGCA TATACCTCGA GTATGTGAAT | 1350 |
| TCTGTCAAGC AGTTTTCCCA CCATCCATTA CATCCAGGGG GGATTTCCTT | 1400 |
| CGGCATCTTA ATTCACACTT CAATGGAGAG ACTTAAGACA CATTTGAAAA | 1450 |
| CAGACATATC AAGTTCTATG TGATGATTTT GGGTTTTTAA TACTATAAAT | 1500 |
| ACTTGATTGT AAACTAAATT CAAGATCATT TATAGGAAAA TCTAGTTTCA | 1550 |
| CAGCTATTTG AATTTTTTTC TGGATTTACT ATATAACTCT TATTTTTTAA | 1600 |
| AAGATCATTC TGTTCTTTCA AGGAGAAATA AGCCTAAAAG AAGAAAAACA | 1650 |
| AAAAAAATTC TGTATAAAAC TGTAATCCTT TGTATTCATG TTTACAGTGC | 1700 |
| TATTACTATA ATTCAAAATT ATGTATGTGA CTTAGAGTTA TATAATCATA | 1750 |
| ATTTATGTTT ATTTCAAATA TCTAAGTTTA TTGCTTGGAT TTCTAGTGAG | 1800 |
| AGCTGTTGAA TTTGGTGATG TCAAATGTTT CTAGGGTTTT TTAGTTTGTT | 1850 |

```
TTTATTGAGA AAATTGATTA TTTATGCTAT AGGTGATATT CTCTTTGAAT            1900

AAACCTATAA TAGGAAATAG CAGACCACAT AAACATCTTT GTAAATATCA            1950

AACCTAATAC ATTTCTTGTC CAGTGATAAA ACAACTGGTA GAATTATTTA            2000

AACACTTTAG ATTTTTAAAT AATAAACATG GCTTTAATTT TTACTGTGTG            2050

TATAGCTACA TGATGAAATT AATTAAATAT TAAGAGGTAA AAAAAAAAAA            2100

AAAAAAAA                                                          2108

(2) INFORMATION FOR SEQ ID NO:7:

(i) SEQUENCE CHARACTERISTICS:
        (A) LENGTH: 1922 base pairs
        (B) TYPE: Nucleic Acid
        (C) STRANDEDNESS: Single
        (D) TOPOLOGY: Linear (xi) SEQUENCE DESCRIPTION: SEQ ID NO:7:

CGGAAAGCTA CTTCCGGTTG CAGTCATTCT GCCGGGCACC GGCGACCTGT              50

GGCGTGAGCG AGCACAGCCG GAACCCTCCA CTAGCTGGCA TTCCTACCAT             100

CCTTTATAGT GATGCTACAG GACAAAGAGG AATGGATAAA AACATTGGTG             150

AGCAACTCAA TAGAGCATAT GAAGCCTTCC GACAGGCATG CATGGATAGA             200

GATTCAGCAG TAAGAGAGCT ACAGCAAAAG CAGACTGAGA ACTATGAACA             250

AAGAATACGC GAGCAACAGG AACAGCTGTC ATTTCAACAA AACCTAATTG             300

ACAGGCTGAA ATCACAGCTA CTTCTCGTGG ATTCTAGTCG AGATAACAGT             350

TATGGCTATG TACCTTTGCT TGAAGACAGT GACAGAAGGA AGAATAATTT             400

GACCCTTGAT GAACCACATG ATAAAGTGAA ACTAGGAACA CTGAGAGATA             450

AGCAATCAAA GGTGAGACGA CAAGAAGTTT CTTCTGGAAA AGAATCCGCC             500

AAGGGTCTCA ACATCCCTCT GCATCACGAA AGGGATAATA TAGAGAAGAC             550

TTTCTGGGAC CTTAAAGAAG AATTTCATAG GATTTGCTTG CTAGCAAAAG             600

CACAGAAAGA TCACTTAAGC AAACTTAATA TACCAGATAT TGCAACTGAC             650

ACACAGTGTT CTGTGCCTAT ACAGTGTACT GATAAAACAG AGAAACAAGA             700

AGCGCTGTTT AAGCCCCAGG CTAAAGATGA TATAAATAGA GGTATGTCGT             750

GCGTCACAGC TGTCACACCA AGAGGACTGG GCCGGGATGA GGAAGATACC             800

TCTTTTGAAT CACTTTCTAA ATTCAATGTC AAGTTTCCGC CTATGGACAA             850

TGACTCTATT TTTCTACATA GCACTCCAGA GGCCCCGAGC ATCCTTGCTC             900

CTGCCACACC TGAGACAGTG TGCCAGGACC GATTTAATAT GGAAGTCAGA             950

GACAACCCAG GAAACTTTGT TAAAACAGAA GAAACTTTAT TTGAAATTCA            1000

GGGAATTGAC CCCATAACTT CAGCTATACA AAACCTTAAA ACAACTGACA            1050

AAACAAACCC CTCAAATCTT AGAGCGACGT GTTTGCCAGC TGGAGACCAC            1100

AATGTGTTCT ATGTAAATAC GTTCCCACTT CAAGACCCGC CTGACGCACC            1150

TTTTCCCTCA CTGGATTCCC CAGGAAAGGC TGTCCGAGGA CCACAGCAGC            1200

CCTTTTGGAA GCCTTTTCTT AACCAAGACA CTGACTTAGT GGTACCAAGT            1250

GATTCAGACT CAGAGCTCCT TAAACCTCTA GTGTGTGAAT CTGTCAAGA             1300

GCTTTTCCCA CCATCCATTA CATCCAGAGG GGATTTCCTC CGGCATCTTA            1350

ATACACACTT TAATGGGGAG ACTTAAATCA CGTTTGAAAA CAGACATATC            1400
```

-continued

| | |
|---|---|
| ATGTTCTCTG TGGTGGTTTT GGATTTGTAA CGCTAGAGAA CGCTTTCTCG | 1450 |
| TGAGCCAAAT GTAAGATTGA TTATAAAGTT GTTACTTTAT CTTTTAAGAG | 1500 |
| ATCATTTTGT ATAGAACTAT AACTCATTAT ATTATTCATG TTTATACCTA | 1550 |
| TAATTTCTAC ATTTCAAAAT TACACATGTG ACTTACAGAG TTATTCAGTC | 1600 |
| ATAATTTATG TTTCAAATAG CTAAGTTTAT TGTTTGACTA TTGTGAGATC | 1650 |
| TATTAAATTT AGTAATAGCA AATGTTTATA GGATATTCAA ATTTCATTTG | 1700 |
| AATTTTTAAT TATTTTTGCT ACAGGTAATA TTCCTTTAAA ATACGTATAT | 1750 |
| AACGTACAGA GAATAACAGA CAATATGATC TAAGTAAATG TCGAATCAAT | 1800 |
| CATTAGTTGC CCAGGGAAAT TTAAACATTA TAGATCATTT TTAAATAATA | 1850 |
| CACATAGTTT TAATTTTTAC TGTGTGTATA GATGCATGAT TAAATGACTT | 1900 |
| AAATATTAAA AAAAAAAAAA AA | 1922 |

(2) INFORMATION FOR SEQ ID NO:8:

(i) SEQUENCE CHARACTERISTICS:
        (A) LENGTH: 2160 base pairs
        (B) TYPE: Nucleic Acid
        (C) STRANDEDNESS: Single
        (D) TOPOLOGY: Linear (xi) SEQUENCE DESCRIPTION: SEQ ID NO:8:

| | |
|---|---|
| CGGCGACCTG TGGCGTGAGC GAGCACAGCC GGAACCCTCC ACTAGCTGGC | 50 |
| ATTCCTACCA TCCTTTATAG TGATGCTACA GGACAAAGAG GAATGGATAA | 100 |
| AAACATTGGT GAGCAACTCA ATAGAGCATA TGAAGCCTTC CGACAGGCAT | 150 |
| GCATGGATAG AGATTCAGCA GTAAGAGAGC TACAGCAAAA GACTGAGAAC | 200 |
| TATGAACAAA GAATACGCGA GCAACAGGAA CAGCTGTCAT TTCAACAAAA | 250 |
| CCTAATTGAC AGGCTGAAAT CACAGCTACT TCTCGTGGAT TCTAGTCGAG | 300 |
| ATAACAGTTA TGGCTATGTA CCTTTGCTTG AAGACAGTGA CAGAAGGAAG | 350 |
| AATAATTTGA CCCTTGATGA ACCACATGAT AAAGTGAAAC TAGGAACACT | 400 |
| GAGAGATAAG CAATCAAAGG TGAGACGACA AGAAGTTTCT TCTGGAAAAG | 450 |
| AATCCGCCAA GGGTCTCAAC ATCCCTCTGC ATCACGAAAG GATAATATA | 500 |
| GAGAAGACTT TCTGGGACCT TAAAGAAGAA TTTCATAGGA TTTGCTTGCT | 550 |
| AGCAAAAGCA CAGAAAGATC ACTTAAGCAA ACTTAATATA CCAGATATTG | 600 |
| CAACTGACAC ACAGTGTTCT GTGCCTATAC AGTGTACTGA TAAAACAGAG | 650 |
| AAACAAGAAG CGCTGTTTAA GCCCCAGGCT AAAGATGATA TAAATAGAGG | 700 |
| TATGTCGTGC GTCACAGCTG TCACACCAAG AGGACTGGGC CGGGATGAGG | 750 |
| AAGATACCTC TTTTGAATCA CTTTCTAAAT TCAATGTCAA GTTTCCGCCT | 800 |
| ATGGACAATG ACTCTATTTT TCTACATAGC ACTCCAGAGG CCCCGAGCAT | 850 |
| CCTTGCTCCT GCCACACCTG AGACAGTGTG CCAGGACCGA TTTAATATGG | 900 |
| AAGTCAGAGA CAACCCAGGA AACTTTGTTA AAACAGAAGA AACTTTATTT | 950 |
| GAAATTCAGG GAATTGACCC CATAACTTCA GCTATACAAA ACCTTAAAAC | 1000 |
| AACTGACAAA ACAAACCCCT CAAATCTTAG AGCGACGTGT TTGCCAGCTG | 1050 |
| GAGACCACAA TGTGTTCTAT GTAAATACGT TCCCACTTCA AGACCCGCCT | 1100 |
| GACGCACCTT TTCCCTCACT GGATTCCCCA GGAAAGGCTG TCCGAGGACC | 1150 |

-continued

```
ACAGCAGGTA ACTGTTTTGC ATTAACAAAT ATTTTATTAT GTGTGAACAC            1200

ACATTTTATC ATACATGTAC AGATACAAAT CTGTTTTAAG TTATCAGGCA            1250

TCCATTTAAA ATTAATGACT ATCCAGAGTT GAGGCTTTCA ATAAAATATG            1300

TAAGTTCTGT ATTCAAGGAC ATGAATTTTG AATGTGACTG CGCTAAAGCT            1350

TCCTTGTGAT ACTGTGGCGT GGCTTTCCCT GCTTCGTCCT CTTCAAGCAC            1400

AGCTTGTTGA CATCAGTGCT CTAATGGATG CTTTATTAAA GTCAGTTACA            1450

GGCAGTAAAT AATTTTTTA AAACTTGTGT AGGTACACAT AATAATGTGT             1500

AATTTTCCAT AAGTAGATAA TTGCACCAAA TATTCAAAAT AAACTGTCAT            1550

TCAGCCTACT TGTGTTACAT TTCTAGTTAC AGCAGTACAG AGGTCTGTAG            1600

TGTTTGGTTT GTTTACTAAC CTGACACTAA GCAGATATCC TTATACAGTT            1650

TTCAAATAAT CCCTGCACAT GAATACTGTA ATCAAATCTC TTCTTTACTG            1700

TTTGTGAAGC ACAAAGACTT TATAGCCCAT GAATCTAATC CTACCATCCT            1750

TTCTTCCAGA TTCAGGTTCT TTCACAGAAA TATTCCTTTT TGTTAGGAAG            1800

AAAAAAAGTT TTGTTTAATT TCTGAAGGTA AATGCTAAGT GTAGAAATGT            1850

TAAAATAAAT AGAAGCATCT CATTAGAACT TTCAAACATT TGATTTTCTA            1900

TCAGATTAAA AAAAATACTT AATACCTTTG GTTTACGTAT TCCTATCAGT            1950

TATAGGCTTT TTGAACAGCA TGGAAAGAAG CAATAGTGAA GCTGTAGGAT            2000

GTCTTAGTAG TGGGCGTAAG TAGAGATTCT GACAAGTCTT AATTATTAAC            2050

TCTCTTATGT TCCACCCTGT ACCTTATTTC ACTTTATGGT CTCAGCTATA            2100

GTTGCTACCA AATGAAACAA TTAAACAATT TCATGTGTTG CGAAAAAAAA            2150

AAAAAAAAAA                                                        2160
```

TRAF INHIBITORS

This is a divisional of non-provisional application Ser. No. 08/700,749 filed Aug. 14, 1996, now U.S. Pat. No. 5,789,550, which claims priority under Section 119(e) to provisional Application Ser. No. 60/002,382 filed Aug. 17, 1985, the entire disclosure of which is hereby incorporated by reference.

FIELD OF THE INVENTION

The present invention concerns the isolation, recombinant production and characterization of novel polypeptides which block signal transduction mediated by tumor necrosis factor associated factors (TRAFs), including TRAF2. In particular, this invention concerns novel proteins that act as specific inhibitors of TRAF2.-dependent NF-κB activation signaled by certain members of the TNF receptor superfamily, such as TNF-R2 and CD40, methods and means for making them and their use in screening assays or as pharmaceuticals.

BACKGROUND OF THE INVENTION

Tumor necrosis factor (TNF) is a cytokine produced mainly by activated macrophages which elicits a wide range of biological effects. These include an important role in endotoxic shock and in inflammatory, immunoregulatory, proliferative, cytotoxic, and anti-viral activities (reviewed by Goeddel, D. V. et al., *Cold Spring Harbor Symposia on Quantitative Biology* 51, 597–609 [1986]; Beutler, B. and Cerami, A., *Ann. Rev. Biochem.* 57, 505–518 [1988]; Old, L. J., *Sci. Am.* 258(5), 59–75 [1988]; Fiers, W. *FEBS Lett.* 285(2), 199–212 [1991]). The induction of the various cellula responses mediated by TNF is initiated by its interaction with two distinct cell surface receptors, an approximately 55 kDa receptortermed TNF-R1 and an approximately 75 kDa receptor termed TNF-R2. Human and mouse cDNAs corresponding to both receptor types have been isolated and characterized (Loetscher, H. et al., *Cell* 61, 351 [1990]; Schall, T. J. et al., *Cell* 61, 361 [1990]; Smith, C. A. et al., *Science* 248, 1019 [1990]; Lewis, M. et al., *Proc. Natl. Acad. Sci. USA* 88, 2830–2834 [1991]; Goodwin, R. G. et al., *Mol. Cell. Biol.* 11, 3020–3026 [1991]. Both TNF-Rs share the typical structure of cell surface receptors including extracellular, transmembrane and intracellular regions. The extracellular portions of both receptors are found naturally also as soluble TNF-binding proteins (Nophar, Y. et al., *EMBO J.* 9, 3269 [1990] and Kohno, T. et al., *Proc. Natl. Acad. Sci. U.S.A.* 87, 8331 [1990]). The amino acid sequence of human TNF-R1 and the underlying nucleotide sequence are disclosed in EP 417,563 (published Mar. 20, 1991), whereas EP 418,014 (published Mar. 20, 1991) discloses the amino acid and nucleotide sequences of human TNF-R2.

Both TNF receptors are independently active in signaling TNF responses. Direct signaling by TNF-R2 has been observed in lymphoid cells in which TNF-R2 stimulates the proliferation of thymocytes and a murine cytotoxic T cell line CT6 (Tartaglia et al., *Proc. Natl. Acad. Sci. USA* 88, 9292–9296 [1991]; Tartaglia et al, *J. Immunol.* 151, 4637–4641 [1993]). Both TNF-R1 and TNF-R2, along with other members of the TNF receptor superfamily, e.g. CD40, have been shown to independently mediate the activation of the transcription factor NF-κB (Lenardo & Baltimore, *Cell* 58: 227–229 [1989]; Laegreid, A., et al.,*J. Biol. Chem.* 269, 7785–7791 [1994]; Rothe et al., *Cell* 78, 681–692 [1994]; Wiegmann et al.,*J. Biol. Chem.* 267, 17997–18001 [1992]). NF-κB is a member of the Rel family of transcriptional activators that control the expression of a variety of important cellular and viral genes (Lenardo & Baltimore, supra, and Thanos and Maniatis, *Cell* 80, 529–532 [1995]). TNF-R2 also mediates the transcriptional induction of the granulocytemacrophage colony stimulating factor (GM-CSF) gene (Miyatake et al., *EMBO J.* 4: 2561–2568 [1985]; Stanley et al., *EMBO J.* 4: 2569–2573 [1985]) and the A20 zinc fingerprotein gene (Opipari et al., *J. Biol. Chem.* 265: 14705–14708 [1990]) in CT6 cells, and participates as an accessory component to TNF-R1 in the signaling of responses primarily mediated by TNF-R1, like cytotoxicity (Tartaglia, L. A. and Goeddel, D. V., *Immunol. Today* 13, 151–153 [1992]).

Recent research has lead to the isolation of polypeptide factors associated with the intracellulardomain of the 75 kDa tumor necrosis factor receptor, TNF-R2 ("tumor necrosis factor receptor associated factors" or "TRAFs") which participate in the TNF-R2 signal transduction cascade. TRAF1 and TRAF2 were the first two identified members of this novel protein family containing a novel C-terminal homology region, the TRAF domain (Rothe et al., *Cell* 78, 681–692 [1994]; U.S. Pat. Nos. 5,670,319 issued on Sep. 23, 1997, and 5,708,142 issued Jan. 13, 1998. A further TRAF domain protein, TRAF3 (originally termed CD40bp, CRAF, or LAP1) has also been identified (Hu et al., *J. Biol. Chem.* 269, 30069 [1994]; Cheng et al., *Science* 267, 1494 [1995], and Mosialos et al., *Cell* 80, 389 [1995]). TRAFs transduce signals from TNF-R2, CD40 and presumably from other members of the TNF receptor superfamily that also includes the low affinity nerve growth factor receptor, the Fas antigen, CD27, CD30, OX40, 4-1BB, and TNFR-RP (Rothe et al., supra; Hu et al., *J. Biol. Chem.* 269, 30069–30072 [1994]; Cheng et al., *Science* 267, 1494–1498 [1995]; Mosialos et al., *Cell* 80, 389–399 [1995]; Rothe et al., *Science*, in press; Smith et al, *Cell* 76, 959–962 [1994]). In addition to the shared conserved C-terminal TRAF domain that is involved in both receptor association and oligomerization, TRAF2 and TRAF3 each contain an N-terminal RING finger domain and five zinc finger structures of weak sequence similarity. CD40 and TNF-R2 interact directly with TRAF2 and indirectly with TRAF1 via a TRAF2/TRAF1 heterodimer. TRAF2 (or the TRAF2/TRAF1 heterodimer) is required for CD40- and TNF-R2-mediated activation of the transcription factor NF-κB. TRAF3 interacts with CD40 and self-associates, but does appear to not associate with TNF-R2, TRAF1, or TRAF2. The role of TRAF3 in signal transduction is less well defined, but it may antagonize the effects of TRAF2 (Rothe et al., *Science*, in press). The TRAF proteins also interact with the C-terminal cytoplasmic domain of the Epstein-Barr virus transforming protein LMP1 (Mosialos et al., *Cell* 80, 389 [1995]). LMP1 is a dominant oncogene that has multiple downstream effects on cell growth and gene expression, at least some of which require NF-κB activation (Laherty et al., *J. Biol. Chem.* 267, 24157 [1992]; Rowe et al.,*J. Virol.* 68, 5602 [1994]). TRAF2 is believed to be a common signal transducer for TNF-R2, CD40 and LMP1.

SUMMARY OF THE INVENTION

The present invention is based on the identification, recombinant production and characterization of certain novel TRAF-interactingproteins named "inhibitors of TRAF" (1-TRAFs). More specifically, the present invention is based on the isolation of cDNAs encoding various forms of murine and human I-TRAFs encoding proteins with no significant sequence similarity to any known protein, and on the expression and characterization of the encoded I-TRAF proteins.

In one aspect, the invention concerns purified I-TRAF proteins which inhibit the interaction of TRAFs with members of the TNF receptor superfamily, such as TNF-R2, CD40, and/or other cellular proteins with which TRAF proteins are normally, directly or indirectly, associated, such as LMP1.

In particular, the invention concerns an isolated I-TRAF polypeptide comprising the amino acid sequence of a polypeptide selected from the group consisting of:

(a) a native sequence I-TRAF polypeptide,
(b) a polypeptidehaving at least about 70% amino acid sequence identity with the TRAF-binding domain of a native sequence I-TRAF polypeptide and capable of inhibiting a TRAF-mediated signaling event, and
(c) a fragment of a polypeptide of (a) or (b) capable of inhibiting a TRAF-mediated signaling event.

Preferably, the I-TRAF polypeptides of the present invention have an at least about 60% overall amino acid sequence identity with a native sequence I-TRAF polypeptide. The I-TRAF polypeptides preferably comprise a fragment of a native mammalian I-TRAF protein that is necessary and sufficient for association with a native TRAF protein. More preferably, the I-TRAF polypeptides comprise a fragment of a native mammalian I-TRAF or a polypeptide sufficiently homologous to retain the ability of interacting with the TRAF domain of a native mammalian TRAF protein. Even more preferably, the I-TRAF polypeptides comprise the N-terminal portion of a native mammalian I-TRAF capable of interaction with a native TRAF, preferably TRAF2. The mammalian proteins are preferably human.

In another aspect, the invention concerns an isolated nucleic acid molecule encoding I-TRAF proteins which inhibit the interaction of TRAFs with members of the TNF receptor superfamily, such as TNF-R2, CD40, and/or other intracellularproteins with which TRAF proteins are normally, directly or indirectly, associated, such as LMP1. The nucleic acid preferably comprises a nucleotide sequence encoding a 413 or 447 amino acid murine I-TRAF protein (SEQ. ID. NOs: 1 and 3) or a 425 amino acid human I-TRAF protein (SEQ. ID. NO: 5) or a functional derivative thereof, including the truncated murine protein shown in FIG. 1 (SEQ. ID. NO: 8). In another preferred embodiment, the nucleic acid is capable of hybridizing to the complement of any of the nucleic acid molecules represented by SEQ. ID. NOs: 2, 4 and 6.

The invention further concerns vectors, cells and organisms comprising such nucleic acid.

In a further aspect, the invention concerns a screening assay for identifying molecules that modulate the I-TRAF/TRAF binding. Preferably, the molecules either prevent I-TRAF/TRAF interaction or prevent or inhibit dissociation of I-TRAF/TRAF complexes. The assay comprises the incubation of a mixture comprising TRAF and I-TRAF with a candidate molecule and detection of the ability of the candidate molecule to modulate I-TRAF/TRAF binding, e.g. to prevent the interaction of I-TRAF with TRAF or to prevent or inhibit the dissociation of I-TRAF/TRAF complexes. The screened molecules preferably are small molecule drug candidates.

In another aspect, the invention relates to an assay for identifying a molecule the signal transduction of which is mediated by the association of a TRAF with a cellular protein, comprising (a) incubating a mixture comprising a TRAF, and an I-TRAF with a candidate molecule, and (b) detecting the ability of the candidate molecule to release TRAF from the complex formed with I-TRAF a TRAF-mediated signaling event.

In yet another aspect, the invention concerns a method of treating a tumor associated with Epstein-Barr virus comprising administering to a patient having developed or at risk of developing such tumor a therapeutically effective amount of an I-TRAF. Pharmaceutical compositions comprising an I-TRAF as an active ingredient are also within the scope of the present invention.

The invention also concerns a method for modulating TRAF-mediated signal transduction in a cell comprising introducing into the cell a nucleic acid encoding an I-TRAF or a functional derivative.

BRIEF DESCRIPTION OF DRAWINGS

FIG. 1(a) shows the deduced amino acid sequences of murine and human I-TRAFs. The translation initiation codons of the murine I-TRAFα and -β splice variants are indicated by α and β, respectively. The splice junction is marked by an asterisk (*). All of the isolated human I-TRAF cDNA clones correspond to murine I-TRAFα. The initiator methionine of human I-TRAF is preceded by an upstream in-frame stop codon not present in the murine I-TRAFα cDNA clones. The amino acid sequences of two additional splice variants of mouse I-TRAFα, ending in premature termination codons, are also listed.

Figure 1B:
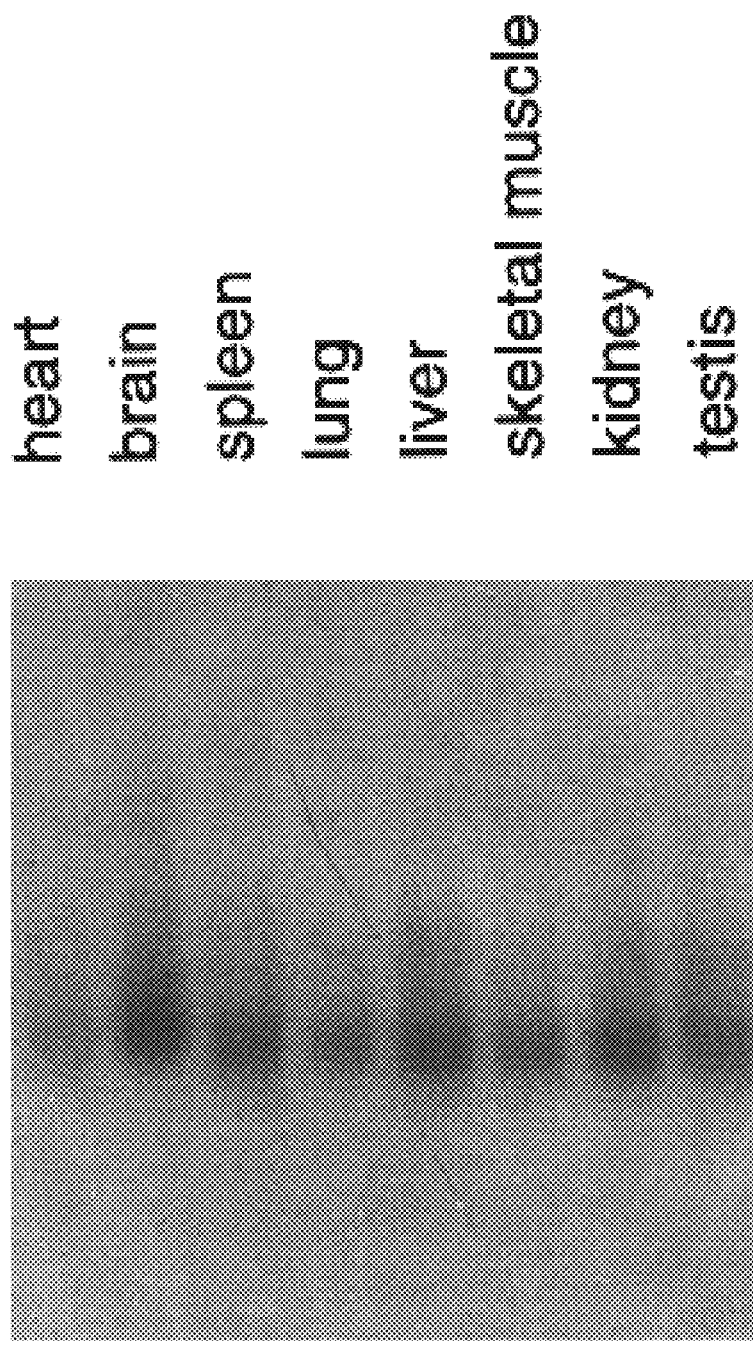
FIG. 1(b) shows the results of Northern blot analysis of I-TRAF mRNA in multiple mouse tissues.
Figure 2:
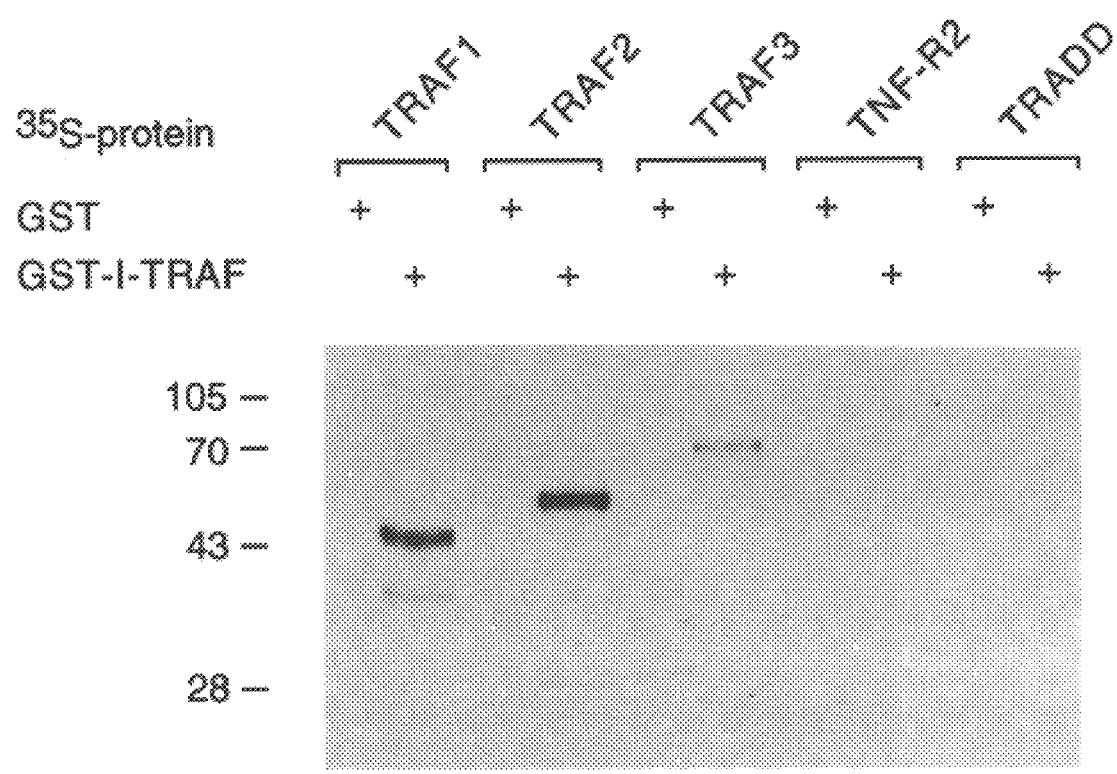
FIG. 2 shows that I-TRAF associates with TRAF 1, TRAF2 and TRAF3 in an in vitro binding assay.

SEQ. ID. NO: 1 shows the amino acid sequence of the 413 aa murine I-TRAF (murine I-TRAFα), starting with the amino acid marked "α" in FIG. 1.

SEQ. ID. NO: 2 shows the nucleotide sequence of murine I-TRAFα. This sequence was obtained from a composite of several independent cloned sequenced.

SEQ. ID. NO: 3 shows the additional 34 amino acids present in the sequence of the 447 aa murine I-TRAF (murine I-TRAFβ), starting with the amino acid marked "β" in FIG. 1.

SEQ. ID. NO: 4 shows the nucleotide sequence encoding the additional 34 amino acids of murine I-TRAFβ.

SEQ. ID. NO: 5 shows the amino acid sequence of full-length human I-TRAF.

SEQ. ID. NO: 6 shows the nucleotide sequence of full-length human I-TRAF.

SEQ. ID. NO: 7 is the complete, unedited nucleotide sequence of one full length clone encoding murine I-TRAFα (clone 8).

SEQ. ID. NO: 8 is the nucleotide sequence encoding the truncated murine I-TRAFα protein ending by the sequence VTVLH shown in FIG. 1 (clone 23).

DETAILED DESCRIPTION OF THE INVENTION

A. Definitions

The phrases "inhibitor of TRAF", "inhibitor of TRAF protein", "inhibitor of TRAF polypeptide", "I-TRAF protein", "I-TRAF polypeptide" and "I-TRAF" are used interchangeably and refer to a native sequence polypeptide which inhibits the interaction of a native TRAF with a cell surface receptor that triggers TRAF-mediated NF-κB activation cascades, such as a member of the TNF receptor superfamily (e.g. TNF-R2, CD40 and/or CD30) and/or with another cellular protein with which the native TRAF is normally (directly or indirectly) associated, provided that such I-TRAF polypeptide is other than a blocking antibody, and functional derivatives thereof. The I-TRAF protein preferably exerts its inhibitory function by binding to a TRAF protein, such as TRAF1, TRAF2 and/or TRAF3, keeping it in a latent state from which the TRAF protein can be released, for example, by ligland-induced receptor aggregation. The phrases "native sequence polypeptide" and "native polypeptide" and their grammatical variants are used interchangeably and designate a polypeptide as occurring in nature in any cell type of any human or non-human animal species, with or without the initiating methionine, whether purified from native source, synthesized, produced by recombinant DNA technology or by any combination of these and/or other methods. Native sequence I-TRAF polypeptides specifically include the 413 amino acid murine I-TRAF (I-TRAFα; SEQ. ID. NO: 1), the 447 amino acid murine I-TRAF (I-TRAFβ; SEQ. ID. NO: 3), and the 425 amino acid human I-TRAF (SEQ. ID. NO: 5), and their additional, naturally occurring alternative splice and allelic variants. Native I-TRAF polypeptides from other mammalian species, such as porcine, canine, equine, etc. are also included.

The phrases "TRAF", "TRAF protein" and "TRAF polypeptide" are used interchangeably and refer to a native sequence factor capable of specific association with the intracellular domain of a native member of the TNF receptor superfamily (such as TNF-R2, CD40 or CD30), and functional derivatives of such native factor. In the context of this definition, the phrase "specific association" is used in the broadest sense, and includes direct binding to a site or region within the intracellular domain of a native TNF receptor superfamily member of the human or of any other animal species, and indirect association mediated by a further molecules,such as anotherTRAF. The phrase "native sequence factor" is defined in an analogous manner to the definition of "native sequence polypeptide" provided above. The native sequence TRAF polypeptides specifically include the native murine TRAF1 and TRAF2 polypeptides disclosed in Rothe el al., Cell 78, 681–692 [1994]), TRAF3 as disclosed in Hu et al., supra; Cheng et al., supra; and Mosialos et al., supra, and their equivalents in human and other animal species.

A "functional derivative" of a native polypeptide is a compound having a qualitative biological activity in common with the native polypeptide. For the purpose of the present invention, a "functional derivative" of a native I-TRAF is defined by its ability to inhibit the association of a TRAF with a member of the TNF receptor superfamily with which the TRAF is naturally associated, with the proviso that such functional derivatives are not (anti-TRAF or anti-TNF receptor superfamily member) blocking antibodies. Preferably, a functional derivative binds to a native TRAF polypeptide, such as TRAF1, TRAF2 and/or TRAF3 thereby (reversibly or irreversibly) preventing its interaction with cell surface receptors (e.g., TNF-R2, CD40, CD30) that trigger TRAF-mediated NF-κB activation cascades. In a particularly preferred embodiment, the prevention of TRAF-mediated signaling is reversible, and the TRAFs can be released from their latent, inhibited state, e.g. by ligand-mediated receptor aggregation. The functional derivatives preferably have at least about 60%, more preferably at least about 70%, even more preferably at least about 80%, most preferably at least about 90% overall amino acid sequence identity with a native sequence I-TRAF polypeptide, preferably a human I-TRAF. Even more preferably, the functional derivatives show at least about 70%, more preferably at least about 80% and most preferably at least about 90% amino acid sequence identity with the TRAF-binding domain of a native sequence I-TRAF polypeptide. Fragments of native sequence I-TRAF polypeptides from various mammalian species and sequences homologous to such fragments constitute another preferred group of I-TRAF functional derivatives. Such fragments preferably include the N-terminal region of a native sequence I-TRAF which is necessary and sufficient for TRAF binding, such as amino acids 35–236 of the mouse I-TRAF sequences represented in SEQ. ID. NO: 1 or 3, and the equivalent part of a human I-TRAF sequence, or show at least about 70%, more preferably at least about 80%, most preferably at least about 90% sequence identity with the TRAF-binding N-terminal portion of a native sequence I-TRAF. Another preferred group of I-TRAF functional derivatives is encoded by nucleic acid hybridizing under stringent conditions to the complement of nucleic acid encoding a native I-TRAF polypeptide.

Functional derivatives of native TRAF polypeptides, as defined for the purpose of the present invention, are characterized by retaining the ability of native TRAFs to associate (directly or indirectly) with the intracellulardomain of a member of the TNF receptor superfamily, such as TNF-R2, CD40 and/or CD30. Such TRAF functional derivatives preferably retain or mimic the region(s) within a native TRAF sequence that directly participate(s) in association with the intracellular domain of a TNF receptor superfamily member and/or in homo- or heterodimerization, along with the region(s) to which a native I-TRAF polypeptide binds. A preferred group of TRAF functional derivatives shows at least about 60%, more preferably at least about 70%, even more preferably at least about 80%, most preferably at least about 90% overall sequence identity with a native sequence TRAF. Other preferred functional derivatives are or comprise the conserved TRAF domains of native sequence TRAF proteins. Within this group, TRAF fragments comprising at least amino acids 264 to 501 of the native TRAF2 amino acid sequence are particularly preferred. Also preferred are TRAF variants which show at least about 70%, more preferably at least about 80%, most preferably at least about 80% amino acid sequence identity with the TRAF region of a native sequence TRAF protein, preferably TRAF2. A further preferred group of TRAF functional derivatives is encoded by nucleic acid capable of hybridizing under stringent conditions to the complement of a native sequence TRAF polypeptide of any mammalian species, including humans.

"Identity" or "homology" with respect to a native polypeptide or polypeptide and its functional derivative herein is the percentage of amino acid residues in the candidate sequence that are identical with the residues of a corresponding native polypeptide, after aligning the sequences and introducing gaps, if necessary, to achieved the maximum percent homology, and not considering any conservative substitutions as part of the sequence identity. Methods and computer programs for the alignment are well known in the art.

"Stringent conditions" can be provided in a variety of ways, such as by overnight incubation at 42° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 μg/ml denatured, sheared salmon sperm DNA. Alternatively, the stringent conditions are characterizedby a hybridization buffer comprising 30% formamidein 5× SSPE (0.18 M NaCl, 0.01 M NaPO₄, pH 7.7, 0.0001 M EDTA) buffer at a temperature of 42° C., and subsequent washing at 42° C. with 0.2× SSPE. Preferably, stringent conditions involve the use of a hybridization buffer comprising 50% formamide in 5×SSPE at a temperature of 42° C. and washing at the same temperature with 0.2× SSPE.

An "isolated" polypeptideor nucleic acid is unaccompaniedwith at least some of the material with which it is associated in its native environment. An isolated polypeptide constitutes at least about 2% by weight, and preferably at least about 5% by weight of the total protein in a given sample. An isolated nucleic acid constitutes at least about 0.5% by weight, and preferably at least about 5% by weight of the total nucleic acid present in a given sample.

The term "antibody" is used in the broadest sense and specifically covers single monoclonal antibodies (including agonist and antagonist antibodies), antibody compositions with polyepitopic specificity, as well as antibody fragments (e.g., Fab, F(ab')₂, and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 256:495 (1975), or may be made by recombinant DNA methods [see, e.g. U.S. Pat. No. 4,816,567 (Cabilly et al.)].

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity [U.S. Pat. No. 4,816,567; Cabilly et al.; Morrison et al., *Proc. Natl. Acad. Sci. USA* 81, 6851–6855 (1984)].

"Humanized" forms of non-human (e.g. murine) antibodies are chimeric immunoglobulins, immunoglobulin chains or fragments thereof (such as Fv, Fab, Fab', F(ab')₂ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody perforrnance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., *Nature* 321, 522–525 (1986); Reichmann et al., *Nature* 332, 323–329 (1988); Presta, *Curr. Op. Struct. Biol.* 2 593–596 (1992) and U.S. Pat. No. 5,225,539 (Winter) issued Jul. 6, 1993.

A "vector" as defined for the purpose of the present invention refers to a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification "plasmid" and "vector" are sometimes used interchangeably as the plasmid is the most commonly used form of vector at present. However, the invention is intended to include such other forms of vectors which serve equivalent functions and which are, or become, known in the art. Preferred expression vectors for mammalian cell culture expression are based on pRK5 (EP 307,247; Rothe et al., *Cell*, supra) and pSVI6B (PCT Publication No WO 91/08291).

In the context of the present invention the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological property, as screened for in the originally transformed cell, are included.

The "host cells" used in the present invention generally are prokaryotic or eukaryotic hosts. Such host cells are, for example, disclosed in U.S. Pat. No. 5,108,901 issued 28 Apr. 1992, and in copending application Ser. No. 08/446,915 filed May 22, 1995 and its parent applications. Suitable prokaryotes include gram negative or gram positive organisms, for example *E. coli* or bacilli. A preferred cloning host is *E. coli* 294 (ATCC 31,446) although other gram negative or gram positive prokaryotes such as *E. coli* B, *E. coli x* 1776 (ATCC 31,537), *E. coli* W3110 (ATCC 27,325), *Pseudomonas* species, or *Serratia Marcesans* are suitable. In addition to prokaryotes, eukaryotic microbes such as filamentous fungi and yeasts are suitable hosts for appropriate vectors of the invention. *Saccharomyces cerevisiae*, or common baker's yeast, is the most commonly used among lower eukaryotic host microorganisms. However, a number of other genera, species and strains are commonly available and useful herein, such as those disclosed in the above-cited patent and patent applications. A preferred yeast strain for the present invention is *Saccharomyces cerevisiae* HF7c (CLONTECH).

Suitable host cells may also derive from multicellularorganisms. Such host cells are capable of complex processing and glycosylation activities. In principle, any higher eukaryotic cell culture is workable, whether from vertebrate or invertebrate culture, although cells from mammals such as humans are preferred. Examples of invertebrate cells include plant and insect cells, see, e.g. Luckow et al., *Bio/Technology* 6, 47–55(1988); Miller et al. in: *Genetic Engineering*, Setlow et al., eds., Vol. 8 (Plenum Publishing, 1986), pp. 277–279; and Maeda et al., Nature 315, 592–594 (1985). Interest has been greatest in vertebrate cells, and propagation of vertebrate cells in culture (tissue culture) is per se known. See, *Tissue Culture*, Academic Press, Kruse and Patterson, eds. (1973). Examples of useful mammalian host cell lines are monkey kidney CV1 line transformed by SV40 (COS-7, ATCC CRL 1651); human embryonic kidney cell line (293 or 293 cells subcloned for growth in suspension culture, Graham et al., *J. Gen. Virol.* 36, 59 [1977]); baby hamster kidney cells 9BHK, (ATCC CCL 10); Chinese hamster ovary cells/-DHFR (CHO, Urlaub and Chasin, *Proc. Natl. Acad. Sci. USA* 77, 4216 [1980]); mouse sertolli cells (TM4, Mather, *Biol. Reprod.* 23, 243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL75); human liver cells (Hep G2, HB 8065); mouse mammary tumor (MMT 060562, ATCC CCL51); TRI cells (Mather et al., *Annals N.Y. Acad. Sci.* 383, 44068 [1982]); MRC 5 cells; FS4 cells; and a human hepatoma cell line (Hep G2). Preferred host cells are human embryonic kidney 293 and Chinese hamster ovary cells. Particularly preferred for the present invention are the murine interleukin-2-dependentcytotoxic T cell line CT6, and the human embryonic kidney cell line 293, which are maintained as described in Tartaglia et al., *Proc. Natl. Acad. Sci. USA* 88, 9292–9296 (1991) and Pennica et al.,*J. Biol. Chem.* 267, 21172–21178 (1992).

"Dissociation" is the process by which two molecules cease to interact: the process occurs at a fixed average rate under specific physical conditions.

B. Identification and Purification of Native I-TRAFs

The native I-TRAF polypeptides may, for example, be identified and purified from certain tissues which possess a TRAF (e.g. TRAF2) mRNA and to express it at a detectable level. Murine I-TRAF can, for example, be obtained from the murine fetal liver stromal cell line 7-4 (FL; Rothe et al., *Cell* supra) or from murine peripheral lymph nodes (PLN; U.S. Pat. No. 5,304,640 issued Apr. 19, 1994). Human I-TRAF can, for example, be purified from human peripheral lymph nodes. I-TRAF mRNA is also present and expressed in brain, spleen, lung, liver, skeletal muscle, kidney and testis tissues (see FIG. 1b), along with TRAF, e.g. TRAF2 mRNAs. Native I-TRAFs can, for example, be identified and purified from tissues expressing their mRNAs based upon their ability to bind TRAF2 (or another TRAF, e.g. TRAF1). Native I-TRAFs will coprecipitated with immunoprecipitated TRAF2. In a preferred embodiment, radiolabeled TRAF2 or a derivative is immunoprecipitated with protein A-agarose (Oncogene Science) or with protein A-Sepharose (Pharmacia). The immunoprecipitate is then analyzed by autoradiography or fluorography, depending on the radiolabel used. The I-TRAF proteins will coprecipitate with the TRAF2 or its derivative, and can be further purified by methods known in the art, such as purification on an affinity column. For large-scale purification a scheme similar to that described by Smith and Johnson, *Gene* 67, 31–40 (1988) can be used. A cell lysate containing the I-TRAF(s) to be purified is applied to a glutathione-S-transferase (GST)-TRAF fusion protein affinity column. Protein(s) bound to the column is/are eluted, precipitated and isolated by SDS-PAGE under reducing conditions, and visualized, e.g. by silver staining. GST gene fusion vectors (pGEX vectors) as well as kits for cloning and expression of GST fusion systems are commercially available from Pharmacia (see Pharmacia Catalog, 1994, pages 133; and 142–143).

C. Recombinant Production of I-TRAF Polypeptides

Preferably, the I-TRAF polypeptides are prepared by standard recombinant procedures by culturing cells transfected to express I-TRAF polypeptide nucleic acid (typically by transforming the cells with an expression vector) and recovering the polypeptide from the cells. However, it is envisioned that the I-TRAF polypeptides may be produced by homologous recombination, or by recombinant production methods utilizing control elements introduced into cells already containing DNA encoding an TRAF polypeptide. For example, a powerful promoter/enhancer element, a suppressor, or an exogenous transcription modulatory element may be inserted in the genome of the intended host cell in proximity and orientation sufficient to influence the transcription of DNA encoding the desired I-TRAF polypeptide. The control element does not encode the I-TRAF polypeptide, rather the DNA is indigenous to the host cell genome. One next screens for cells making the polypeptide of this invention, or for increased or decreased levels of expression, as desired. General techniques of recombinant DNA technology are, for example, disclosed in Sambrook et al., *Molecular Cloning: A laboratory Manual*, Second Edition (Cold Spring Harbor, N.Y.: Cold Spring Harbor Laboratory Press) 1989.

1. Isolation of DNA Encoding the I-TRAF Polypeptides

For the purpose of the present invention, DNA encoding a I-TRAF polypeptide may, for example, be obtained from CDNA libraries prepared from tissue believed to possess a TRAF mRNA and to express it at a detectable level. For example, cDNA library can be constructed by obtaining polyadenylatedmRNA from a cell line known to express a TRAF protein, and using the mRNA as a template to synthesize double stranded cDNA. Human and non-human cell lines and tissues suitable for this purpose have been listed hereinabove. Alternatively, DNA encoding new I-TRAF polypeptides can be obtained from cDNA libraries prepared from tissue known to express a previously identified I-TRAF polypeptide at a detectable level. The I-TRAF polypeptide genes can also be obtained from a genomic library, such as a human genomic cosmid library.

Libraries, either cDNA or genomic, are screened with probes designed to identify the gene of interest or the protein encoded by it. For cDNA expression libraries, suitable probes include monoclonal and polyclonal antibodies that recognize and specifically bind to an I-TRAF polypeptide. For cDNA libraries, suitable probes include carefully selected oligonucleotide probes (usually of about 20–80 bases in length) that encode known or suspected portions of an I-TRAF polypeptide from the same or different species, and/or complementary or homologous cDNAs or fragments thereof that encode the same or a similar gene. Appropriate probes for screening genomic DNA libraries include, without limitation, oligonucleotides, cDNAs, or fragments thereof that encode the same or a similar gene, and/or homologous genomic DNAs or fragments thereof. Screening the cDNA or genomic library with the selected probe may be conducted using standard procedures as described in Chapters 10–12 of Sambrook et al., *Molecular Cloning: A Laboratory Manual*, New York, Cold Spring Harbor Laboratory Press, (1989).

A preferred method of practicing this invention is to use carefully selected oligonucleotide sequences to screen cDNA libraries from various tissues. The oligonucleotide sequences selected as probes should be sufficient in length and sufficiently unambiguous that false positives are minimized. The actual nucleotide sequence(s) is/are usually designed based on regions of an I-TRAF which have the least codon redundancy. The oligonucleotides may be degenerate at one or more positions. The use of degenerate oligonucleotides is of particular importance where a library is screened from a species in which preferential codon usage is not known.

The oligonucleotide must be labeled such that it can be detected upon hybridization to DNA in the library being screened. The preferred method of labeling is to use ATP (e.g., $\gamma^{32}P$) and polynucleotide kinase to radio label the 5' end of the oligonucleotide. However, other methods may be used to label the oligonucleotide, including, but not limited to, biotinylation or enzyme labeling.

cDNAs encoding I-TRAFs can also be identified and isolated by other known techniques of recombinant DNA technology, such as by direct expression cloning or by using the polymerase chain reaction (PCR) as described in U.S. Pat. No. 4,683,195, issued Jul. 28, 1987, in section 14 of Sambrook et al., *Molecular Cloning: A Laboratory Manual*, second edition, Cold Spring Harbor Laboratory Press. New York, 1989, or in Chapter 15 of *Current Protocols in Molecular Biology*, Ausubel et al. eds., Greene Publishing Associates and Wiley-Interscience 1991. This method requires the use of oligonucleotide probes that will hybridize to DNA encoding an I-TRAF.

According to a preferred method for practicing the invention, the coding sequences for I-TRAF proteins can be identified in a recombinant cDNA library or a genomic DNA library based upon their ability to interact with TRAF proteins, e.g. TRAF2. For this purpose one can use the yeast genetic system described by Fields and co-workers [Fields and Song, *Nature* (*London*) 340, 245–246 (1989); Chien et al., *Proc. Natl. Acad. Sci. USA* 88, 9578–9582 (1991)] as disclosed by Chevray and Nathans [*Proc. Natl. Acad. Sci. USA* 89, 5789–5793 (1992)]. Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybridtechnique is commercially available from Clontech. This system can also be extended to map protein domains involved in specific protein interactions as well as to pinpoint amino acid residues that are crucial for these interactions. Yeast two-hybrid cloning can be performed as described in Rothe et al., supra, using TRAF2 or its TRAF domain in the GAL4 DNA-binding domain vector pPC97 (Chevray and Nathans, supra) as bait.

Once the sequence is known, the gene encoding a particular I-TRAF polypeptide can also be obtained by chemical synthesis, following one of the methods described in Engels and Uhlmann, *Angew. Chem. Int. Ed. Engl.* 28, 716 (1989). These methods include triester, phosphite, phosphoramidite and H-phosphonate methods, PCR and other autoprimer methods, and oligonucleotide syntheses on solid supports.

2. Amino Acid Sequence Variants of Native I-TRAF Proteins or Fragments

Amino acid sequence variants of native I-TRAFs and I-TRAF fragments are prepared by methods known in the art by introducing appropriate nucleotide changes into a native or variant I-TRAF DNA, or by in vitro synthesis of the desired polypeptide. There are two principle variables in the constructions of amino acid sequence variants: the location of the mutation site and the nature of the mutation. With the exception of naturally-occurring alleles, which do not require the manipulation of the DNA sequence encoding the I-TRAF, the amino acid sequence variants of I-TRAF polypeptides are preferably constructed by mutating the DNA, either to arrive at an allele or an amino acid sequence variant that does not occur in nature. Methods for identifying target residues within native proteins and for making amino acid sequence variants are well known in the art, and are, for example, disclosed in U.S. Pat. No. 5,108,901 issued Apr. 28, 1992, and in copending application Ser. No. 08/446,915 filed May 22, 1995 and its parent applications. The preferred techniques include alanine-scanning mutagenesis, PCR mutagenesis, cassette mutagenesis, the phageamid display method, details of which are also found in general textbooks, such as, for example, Sambrook et al., sura, and Current Protocols in Molecular Biology, Ausubel et al., eds., supra.

A preferred group of the I-TRAF amino acid sequence variants of the present invention comprises the substitution, insertion and/or deletion of one or more amino acids in a region directly involved in TRAF-binding. Amino acid alterations within this region are expected to result in genuine changes in the I-TRAF/TRAF binding affinity and may yield variants with stronger or weaker binding affinity than native I-TRAFs, as desired.

Naturally-occurring amino acids are divided into groups based on common side chain properties:
(1) hydrophobic: norleucine, met, ala, val, leu, ile;
(2) neutral hydrophobic: cys. ser, thr;
(3) acidic: asp, glu;
(4) basic: asn, gin, his, lys, arg;
(5) residues that influence chain orientation: gly, pro; and
(6) aromatic: trp, tyr, phe.

Conservative substitutions involve exchanging a member within one group for another member within the same group, whereas non-conservative substitutions will entail exchanging a member of one of these classes for another. Variants obtained by non-conservative substitutions are expected to result in more significant changes in the biological properties/function of the obtained variant.

Amino acid sequence deletions generally range from about 1 to 30 residues, more preferably about 1 to 10 residues, and typically are contiguous. Deletions are preferably introduced into regions not directly involved in the interaction with TRAF, although deletions, optionally in combination with other types of mutations, in the TRAF-binding domain are also contemplated.

Amino acid insertions include amino- and/or carboxyl-terminal fusions ranging in length from one residue to polypeptides containing a hundred or more residues, as well as intrasequence insertions of single or multiple amino acid residues. Intrasequence insertions (i.e. insertions within the I-TRAF protein amino acid sequence) may range generally from about 1 to 10 residues, more preferably 1 to 5 residues, more preferably 1 to 3 residues. Examples of terminal insertions include the I-TRAF polypeptides with an N-terminal methionyl residue, an artifact of its direct expression in bacterial recombinant cell culture, and fusion of a heterologous N-terminal signal sequence to the N-terminus of the I-TRAF molecule to facilitate the secretion of the mature I-TRAF from recombinant host cells. Such signal sequences will generally be obtained from, and thus homologous to, the intended host cell species. Suitable sequences include STII or Ipp for *E. coli*, alpha factor for yeast, and viral signals such as herpes gD for mammalian cells.

Other insertional variants of the native I-TRAF molecules include the fusion of the N- or C-terminus of the I-TRAF molecule to immunogenic polypeptides, e.g. bacterial polypeptides such as beta-lactamase or an enzyme encoded by the *E. coli* trp locus, or yeast protein, and C-terminal fusions with proteins having a long half-life such as immunoglobulin regions (preferably immunoglobulin constant regions to yield immunoadhesins), albumin, or ferritin, as described in WO 89/02922 published on Apr. 6, 1989. For the production of immunoglobulin fusions see also U.S. Pat. No. 5,428,130 issued Jun. 27, 1995.

Since it is often difficult to predict in advance the characteristics of a variant TRAF, it will be appreciated that screening will be needed to select the optimum variant. For this purpose biochemical or other screening assays, such as those described hereinbelow, will be readily available.

Preferred amino acid sequence variants of native sequence I-TRAF polypeptides have the sequences not required for TRAF-binding (e.g. most of amino acids from position 237 to the C-terminus of the murine I-TRAF sequence) deleted, leaving the TRAF-interacting region as the sole functionally intact domain. Such variants may additionally have amino acid substitutions, insertions and/or deletions within the TRAF-interacting region, in order to optimize their binding properties, stability or other characteristics.

3. Insertion of DNA into a Cloning/Expression Vehicle

Once the nucleic acid of a native or variant I-TRAF is available, it is generally ligated into a replicable expression vector for further cloning (amplification of the DNA) or expression.

Expression and cloning vectors are well known in the art and contain a nucleic acid sequence that enables the vector to replicate in one or more selected host cells. The selection of an appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence. Suitable expression vectors, for use in combination with a variety of host cells, are well known in the art, and their preferred representatives have been listed hereinabove.

The host cells are then transformed, cultured, and the gene amplification/expression is detected by methods well known in the art, such as those disclosed in Sambrook et al., supra, and Ausubel et al., supra.

4. Isolation and Purification of the I-TRAF Polypeptides

The I-TRAF polypeptides are typically recovered from lysates of recombinant host cells. When I-TRAF is expressed in a recombinant host cell other than one of human origin, it is completely free of proteins or polypeptides of human origin. However, it is necessary to purify the I-TRAF protein from recombinant cell proteins or polypeptides to obtain preparations that are substantially homogenous to the I-TRAF. As a first step, the culture medium or lysate is centrifuged to remove particulate cell debris. The membrane and soluble fractions are then separated. The I-TRAF protein may then be purified from the soluble protein fraction. The following procedures are exemplary of suitable purification procedures: fractionation or immunoaffinity on ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; and protein A Sepharose columns to remove contaminant such as IgG. The preferred scheme for purifying native I-TRAFs from cells in which they naturally occur is equally suitable for the purification of recombinant I-TRAFs, including functional derivatives of the native molecules, from recombinant host cells.

D. Covalent Modifications of I-TRAF Polypeptides

Covalent modifications of I-TRAF are included within the scope herein. Such modifications are traditionally introduced by reacting targeted amino acid residues of the I-TRAF with an organic derivatizing agent that is capable of reacting with selected sides or terminal residues, or by harnessing mechanisms of post-translational modifications that function in selected recombinant host cells. The resultant covalent derivatives are useful in programs directed at identifying residues important for biological activity, for immunoassays of the I-TRAF, or for the preparation of anti-I-TRAF antibodies for immunoaffinity purification. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyldisulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid, O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $PK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R'—N=C=N—R') such as I-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylationof hydroxyl groups of seryl, threonyl or tyrosyl residues, methylation of the α-amino groups of lysine, arginine, and histidine side chains (T. E. Creighton, *Proteins: Structure and Molecular Properties*, W. H. Freeman & Co., San Francisco, pp. 79–86 [1983]), acetylation of the N-terminal amine, and amidation of any C-terminal carboxyl group. The molecules may further be covalently linked to nonproteinaceous polymers, e.g. polyethylene glycol, polypropylene glycol or polyoxyalkylenes, in the manner set forth in U.S. Ser. No. 07/275,296 or U.S. Pat. Nos. 4,640,835; 4,496,689; 4,301,144; 4,670,417; 4,791,192 or 4,179,337.

Derivatization with bifunctional agents is useful for preparing intramolecular aggregates of I-TRAFs with polypeptides as well as for cross-linking the I-TRAF polypeptide to a water insoluble support matrix or surface for use in assays or affinity purification. In addition, a study of interchain cross-links will provide direct information on conformational structure. Commonly used cross-linking agents include 1,1-bis(diazoacetyl)-2-phenylethaneglutaraldehyde, N-hydroxysuccinimide esters, homobifunctional imidoesters, and bifunctional maleimides. Derivatizing agents such as methyl-3-[(p-azidophenyl)dithio]propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl, threonyl or tyrosyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)].

The TRAF may be entrapped in microcapsules prepared, for example, by coacervation techniques or by interfacial polymerization, in colloidal drug delivery systems (e.g. liposomes, albumin microspheres, microemulsions, nano-particles and nanocapsules), or in macroemulsions. Such techniques are disclosed in *Remington's Pharmaceutical Sciences*, 16th Edition, Osol, A., Ed. (1980).

E. Use of I-TRAF Polypeptides and Nucleic Acid Encoding Them

The nucleic acids encoding the I-TRAF polypeptides of the present invention find a variety of applications on their own, including use as translatable transcripts, hybridization probes for identifying nucleic acid encoding I-TRAFs from other species and/or structurally related polypeptides, PCR primers, and therapeutic nucleic acids, including gene therapy applications. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83, 4143–4146 [1986]). The oligonucleotides can be modified to enhance their uptake, e.g. by substituting their negatively charged phosphodiester groups by uncharged groups.

There are a variety of techniques available for introducing nucleic acids into viablecells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellularhalf-life. The technique of receptor-mediatedendocytosis is described, for example, by Wu et al., *J. Biol. Chem.* 262, 4429–4432 (1987); and Wagner et al., *Proc. Natl. Acad. Sci. USA* 87, 3410–3414 (1990). For review of the currently known gene marking and gene therapy protocols see Anderson et al., *Science* 256, 808–813 (1992).

The I-TRAF polypeptides are useful in assays for identifying lead compounds for therapeutically active agents that modulate I-TRAF/TRAF binding. Specifically, lead compounds that either prevent the formation of I-TRAF/TRAF complexes or prevent or inhibit dissociation of the I-TRAF/TRAF complexes already formed can be conveniently identified. Molecules preventing the interaction of I-TRAF and TRAF may find utility under circumstances when boosting of the immune system is desirable. Inhibitors of the dissociation of I-TRAF/TRAF complexes may be useful as immunosuppressants or antiinflammatory agents. Screening assays can also be designed to find lead compounds that mimic the biological activity of a native ligand of a TNF receptor superfamily member with which a TRAF protein is associated, e.g. TNF, CD40 ligand, CD30 ligand, etc. These screening methods involve assaying the candidate agents for their ability to release TRAFs from I-TRAF inhibition.

The screening assays of the present invention are amenable to high-throughput screening of chemical libraries, and are particularly suitable for identifying small molecule drug candidates. Small molecules, which are usually less than 10 K molecular weight, are desirable as therapeutics since they are more likely to be permeable to cells, are less susceptible to degradation by various cellular mechanisms, and are not as apt to elicit an immune response as proteins. Small molecules include but are not limited to synthetic organic or inorganic compounds. Many pharmaceutical companies have extensive libraries of such molecules, which can be conveniently screened by using the assays of the present invention.

The assays can be performed in a variety of formats, including protein-protein binding assays, biochemical screening assays, immunoassays, cell based assays, etc. Such assay formats are well known in the art.

The assay mixture typically contains an I-TRAF and a TRAF protein with which I-TRAF is normally associated (e.g. TRAF2 or TRAF3), usually in an isolated, partially pure or pure form. One or both of these components may be fused to another peptide or polypeptide, which may, for example, provide or enhance protein-proteinbinding, improve stability under assay conditions, etc. In addition, one of the components usually comprises or is coupled to a detectable label. The label may provide for direct detection by measuring radioactivity, luminescence, optical or electron density, etc., or indirect detection such as an epitope tag, an enzyme, etc. The assay mixture additionally comprises a candidate pharmacological agent, and optionally a variety of other components, such as salts, buffers, carrier proteins, e.g. albumin, detergents, protease inhibitors, nuclease inhibitors, antimicrobial agents, etc., which facilitate binding, increase stability, reduce non-specific or background interactions, or otherwise improve the efficiency or sensitivity of the assay.

To screen for inhibitors of I-TRAF/TRAF binding, the assay mixture is incubated under conditions whereby, but for the presence of the candidate pharmacological agent, the I-TRAF specifically binds the TRAF protein with a reference binding affinity. The mixture components can be added in any order that provides for the requisite binding. Incubation may be performed at any temperature which facilitates optimal binding, typically between about 4° and 40° C., more commonly between about 15° and 40° C. Incubation periods are likewise selected for optimal binding but also minimized to facilitate rapid, high-throughput screening, and are typically between about 0.1 and 10 hours, preferably less than 5 hours, more preferably less than 2 hours. After incubation, the effect of the candidate pharmacological agent on the I-TRAF/TRAF binding is determined in any convenient way. For cell-free binding-type assays, a separation step is often used to separate bound and unbound components. Separation may, for example, be effected by precipitation (e.g. TCA precipitation, immunoprecipitation, etc.), immobilization (e.g. on a solid substrate), followed by washing. The bound protein is conveniently detected by taking advantage of a detectable label attached to it, e.g. by measuring radioactive emission, optical or electron density, or by indirect detection using, e.g. antibody conjugates.

Compounds which inhibit or prevent the dissociation of the I-TRAF/TRAF complexes can be conveniently identified by forming the I-TRAF/TRAF complex in the absence of the candidate pharmacological agent, adding the agent to the mixture, and changing the conditions such that, but for the presence of the candidate agent, TRAF would be released from the complex. This can, for example, be achieved by changing the incubation temperature or by adding to the mixture a compound which, in the absence of the candidate pharmacological agent, would release TRAF from its complexed form. As an example, this compound can be a native ligand the signal transduction of which is mediated by TRAF, e.g. TNF, a CD40 ligand, a CD30 ligand, etc. The concentration of the free or bound TRAF can then be detected and/or the dissociation constant of the I-TRAF/TRAF complex can be determined and compared with that of the control.

In order to identify lead compounds for therapeutically active agents that mimic the biological activity of a native ligand of a TNF receptor superfamily member with which a TRAF protein is associated (e.g. TNF, CD40 ligand, CD30 ligand, etc.), the candidate agent is added to a mixture of I-TRAF and TRAF (e.g. TRAF2 or TRAF3). The mutual ratio of the TRAF protein and the cellular protein and the incubation conditions are selected such that I-TRAF/TRAF complexes are formed prior to the addition of the candidate agent. Upon addition of a candidate agent, its ability to release TRAF from the I-TRAF/TRAF complex is tested. The typical assay conditions, e.g. incubation temperature, time, separation and detection of bound and unbound material, etc. are as hereinabove described. In a particular version of this assay, the assay mixture additionally contains a cellular protein with which the TRAF is normally associated (e.g. TNF-R2 or CD40), and the mutual ratio of the TRAF protein and the cellular protein and the incubation conditions are selected such that TRAF signaling does not occur prior to the addition of the candidate ligand analog. Upon addition of the candidate molecule, its ability to initiate a TRAF-mediated signaling event is detected. As an end point, it is possible to measure the ability of a candidate agent to induce TRAF-mediated NF-κB activation in a conventional manner. According to a preferred method, an NF-κB-dependent reporter gene, such as an E-selecting-luciferase reporter construct (Schindler and Baichwal, *Mol. Cell. Biol.* 14, 5820 [1994]), is used in a cell type assay. Luciferase activities are determined and normalized based on β-galactosidase expression. Alternatively, NF-κB activation can be analyzed by electrophoretic mobility shift assay (Schütze et al., *Cell* 71, 765–776 [1992]). However, other conventional biochemical assays are equally be suitable for detecting the release of TRAF from its complexed (and inhibited) form.

Based upon their ability to bind TRAFs. the I-TRAF polypeptides of the present invention can be used to purify native and variant TRAFs and their functional derivatives, which, in turn, are useful for the purification of TNF-R2, CD40 and other members of the TNF receptor superfamily to which they specifically bind. Members of the TNF receptor superfamily are promising candidates for the treatment of a variety of pathological conditions, for example, TNF-R2 (either as a soluble protein or as a TNF-R2-Ig immunoadhesin) is in clinical trials for the treatment of endotoxic (septic shock) and rheumatoid arthritis (RA).

The I-TRAF molecules of the present invention may additionally be used to generate blocking (antagonist) or agonist anti-I-TRAF antibodies, which block or mimic the ability of I-TRAF to inhibit TRAF-mediated signal transduction. Generic methods for generating antibodies are well known in the art and are, for example, described in the textbooks and other literature referenced hereinbefore in connection with the definition of antibodies and concerning general techniques of recombinant DNA technology.

The I-TRAF molecules (including functional derivatives of native I-TRAFs) are also useful as therapeutics for the treatment of pathological conditions associated with downstream effects of the oncogene LMP1 on cell growth and gene expression. LMP1 is an Epstein-Barr virus transforming protein which is believed to play an important role in the development of tumors associated with EB virus, such as Burkitt's lymphoma (cancer of B lymphocytes) which has high incidence in West Africa and Papua New Guinea, and nasopharyngeal carcinoma, which is most common in Southern China and Greenland. Based upon their ability to block TRAF-mediated signaling through LMP1, the I-TRAFs of the present invention may inhibit the downstream effects of LMP1, including LMP1-mediated NF-κB activation, and are, optionally in combination with other cancer therapies, promising agents for the treatment of these types of cancers.

The in vivo efficacy of the treatment of the present invention can be studied against chemically induced tumors in various rodent models. Tumor cell lines propagated in in vitro cell cultures can be introduced in experimental rodents, e.g. mice by injection, for example by the subcutaneous route. Techniques for chemical inducement of tumors in experimental animals are well known in the art.

The treatment of the present invention may be combined with known tumor therapies, such as radiation therapy, chemotherapy, and immunotoxin therapy.

Therapeutic compositions comprising the I-TRAF polypeptides of the present invention, including functional derivatives, are prepared for storage by mixing the active ingredient having the desired degree of purity with optional physiologically acceptable carriers, excipients or stabilizers (Remington's Pharmaceutical Sciences 16th Edition, Osol, A. Ed. 1980) in the form of lyophilized formulations or aqueous solutions. Acceptable carriers, excipients or stabilizers are nontoxic to recipients at the dosages and concentrationsemployed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

The active ingredients may also be entrapped in microcapsules prepared, for example, by coacervation techniques or by interfacial polymerization, for example, hydroxymethylcellulose or gelatin-microcapsulesand poly-(methylmethacylate)microcapsules, respectively), in colloidal drug delivery systems (for example, liposomes, albumin microspheres, microemulsions, nano-particles and nanocapsules) or in macroemulsions. Such techniques are disclosed in *Remington's Pharmaceutical Sciences*, supra.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Suitable examples of sustained release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (U. Sidman et al., *Biopolymers* 22 (1): 547–556 [1983]), poly (2-hydroxyethyl-methacrylate) (R. Langer, et al., *J. Biomed. Mater. Res.* 15: 167–277 [1981] and R. Langer, *Chem. Tech.* 12: 98–105 [1982]), ethylene vinyl acetate (R. Langer et al., Id.) or poly-D-(−)-3-hydroxybutyric acid (EP 133,988). Sustained release compositions also include liposomes. Liposomes containing a molecule within the scope of the present invention are prepared by methods known per se: DE 3,218,121; Epstein et al., *Proc. Natl. Acad. Sci. USA* 82: 3688–3692 (1985); Hwang et al., *Proc. Natl. Acad. Sci. USA* 77: 4030–4034 (1980); EP 52322; EP 36676A; EP 88046; EP 143949; EP 142641; Japanese patent application 83-118008; U.S. Pat. Nos. 4,485,045 and 4,544,545; and EP 102,324. Ordinarily the liposomes are of the small (about 200–800 Angstroms) unilamelar type in which the lipid content is greater than about 30 mol. % cholesterol, the selected proportion being adjusted for the optimal NT-4 therapy.

An effective amount of the active ingredient will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 μg/kg to up to 100 mg/kg or more, depending on the factors mentioned above. Typically, the clinician will administer a molecule of the present invention until a dosage is reached that provides the required biological effect. The progress of this therapy is easily monitored by conventional assays.

Further details of the invention will be apparent from the following non-limiting examples.

EXAMPLE 1

Cloning of Murine and Human I-TRAFs

I-TRAF was identified in a yeast two-hybrid screening system (Fields and Song, *Nature* 340, 245–246 [1989]) as described (Rothe et al., *Cell* 78 681–692 [1994]), using full length TRAF2 in the GAL4 DNA-binding domain vector pPC97 (Chevray and Nathans, *Proc. Natl. Acad. Sci. USA* 89, 5789–5793 [1992]) as bait. A plasmid cDNA library in the GAL4 transcriptional activation domain vector pPC86 (Chevray and Nathans, supra) was constructed from SalI-NotI-adapted, double-stranded fetal liver stromal cell line 7-4 cDNA (FL, Rothe et al., supra) and murine peripheral lymph nodes (PLN; provided by P. Young, D. Dowbenko, and L. Lasky; U.S. Pat. No. 5,304,640 issued Apr. 19, 1994). Transformation efficiencies for the two libraries were 10 and 1 million, respectively. Restriction mapping of 24 positive clones indicated that most were derived from the same gene. Four FL and two PLN cDNA clones were sequenced on a 373A automated DNA sequencer (Applied Biosystems). The 5' ends of six additional murine I-TRAF DNA clones isolated by screening a CT6 cDNA library prepared in λgt22a were also sequenced (Rothe et al., supra). The isolated cDNAs corresponded to several distinct transcripts of the murine I-TRAF gene. Due to alternative splicing, these transcripts have the potential to utilize two different translation initiation codons. The two major forms of murine I-TRAF mRNA are predicted to encode proteins of 413 and 447 amino acids that we have termed I-TRAFα and I-TRAFβ, respectively (FIG. 1a; SEQ. ID. NOs: 1 and 2).

Five human I-TRAF c-DNA clones, obtained by screening a λgt11 HUVEC cDNA library (Hsu et al., *Cell* 81, 495–504 [1995]) with a murine I-TRAF probe, were sequenced. All isolated human I-TRAF cDNAs encode a full length 425 amino acid protein ($M_r$ 48 K) that shows a 82% amino acid identity to murine I-TRAFα (FIG. 1a). Database searches failed to reveal any proteins having significant sequence similarity to I-TRAF. Northern blot analysis using mRNA from mouse tissues indicated that the ~2.4 kb I-TRAF mRNA is ubiquitously expressed (FIG. 1b). The multiple tissue blot (Clontech) was hybridized with a murine I-TRAF cDNA probe according to the Clontech protocol. I-TRAF mRNA is the band at ~2.4 kb.

Murine and human I-TRAF CDNA sequences have been deposited in GenBank and in the American Type Culture Collection (ATCC), 12301 Parklawn Drive, Rockville, Md., USA, under accession numbers and, respectively.

EXAMPLE 2

Characterization of I-TRAF (1) Two-hybrid Binding Assay

Inspection of the various I-TRAF eDNAs obtained by two-hybrid screening indicated that the N-terminal portion of murine I-TRAF (amino acids 35–236) is sufficient for interaction with TRAF2. Further two-hybrid experiments were performed to determine which portion of TRAF2 is required for interaction with I-TRAF. Yeast HF7c cells were cotransformed with an expression vector encoding a Gal14 activation domain-I-TRAF fusion protein and the indicated Gal4 DNA-binding domain expression vectors (Rothe et al., supra). Each transformation mixture was plated on a synthetic dextrose plate lacking leucine and tryptophan. Filter assays for β-galactosidase activity were performed to detect interaction between fusion proteins (Fields and Song, supra). The data are presented in Table 1 below.

TABLE 1

Interactions between I-TRAF and TRAFs, TNF-R2

| DNA-binding domain hybrid | Activation domain hybrid | Interaction* |
|---|---|---|
| — | I-TRAF | − |
| TRAF1 | I-TRAF | ++ |
| TRAF2 | I-TRAF | ++ |
| TRAF2(87–501) | I-TRAF | ++ |
| TRAF3 | I-TRAF | + |
| TNF-R2 | I-TRAF | − |

*Double plus and plus signs indicate strong blue color development within 30 minutes and one hour of the assay, respectively. Minus sign indicates no development of color within 24 hours.

The results show that only the conserved TRAF domain (amino acids 264–501) of TRAF2 is required for interaction with I-TRAF. Furthermore, both TRAF1 and TRAF3 also associate with I-TRAF.

(2) In Vitro Binding Assay

The interactions of $^{35}$S-labeled TRAF1 (Rothe et al., supra), TRAF2 (Rothe et al., supra), TRAF3 (Hu et al., supra), TNF-R2 (Smith et al., *Science* 248, 1019–1023 [1990]), and TRADD (Hsu et al., *Cell* 81, 495–504 [1995]) with I-TRAFα expressed as a glutathione-S-transferase (GST) fusion protein (GST-I-TRAF) and control GST protein were examined. GST-I-TRAF was expressed using the pGEX3X vector (Pharmacia) and purified as described (Smith and Johnson, *Gene* 67, 31–40 [1988]). $^{35}$S-labeled proteins were generated using TNT coupled reticulocyte lysate system (Promega) and the various cDNAs cloned in pBluescript KS (Stratagene) or pRK5 (Schall et al., *Cell* 61, 361–370 [1990]). For each binding assay, 0.5 μg GST-I-TRAF or 0.5 μg GST bound to glutathione Sepharose beads was incubated with equivalent cpm of the individual $^{35}$S-labeled proteins in 1 ml of E1A buffer (50 mM HEPES [pH 7.6], 250 mM NaCl, 0.1% NP-40, 5 mM EDTA) at 4° C. for 1 hour. Beads were washed six times with E1A buffer and precipitates were fractionated by 10% SDS-PAGE. The gel was dried and exposed to Kodak X-ray film. By this assay, I-TRAF was found to specifically interact with TRAF1, TRAF2, and TRAF3.

Results from both two-hybrid and in vitro binding experiments show that I-TRAF interacts more strongly with TRAF1 and TRAF2 than with TRAF3.

(3) Three-hybrid Interaction Test

I-TRAF does not directly interact with TNF-R2 (Table 1). However, as TRAF1 and TRAF2 form a complex with TNF-R2, it was important to ask if I-TRAF can indirectly associate with TNF-R2 via TRAFs. A three-hybrid interaction test (Rothe et al., supra) was performed to address this question. Whereas TRAF2 can bind simultaneously to TRAF1 and TNF-R2 (Rothe et al., supra), it was not able to mediate I-TRAF interaction with TNF-R2. In fact, I-TRAF expression in yeast was found to inhibit the association of TRAF2 with TNF-R2 (data not shown). This result is consistent with I-TRAF and TNF-R2 both binding to the same C-terminal TRAF domain of TRAF2.

(4) Inhibition of TRAF2:TNF-R2 Interaction in Mammalian Cells

Figure 3:
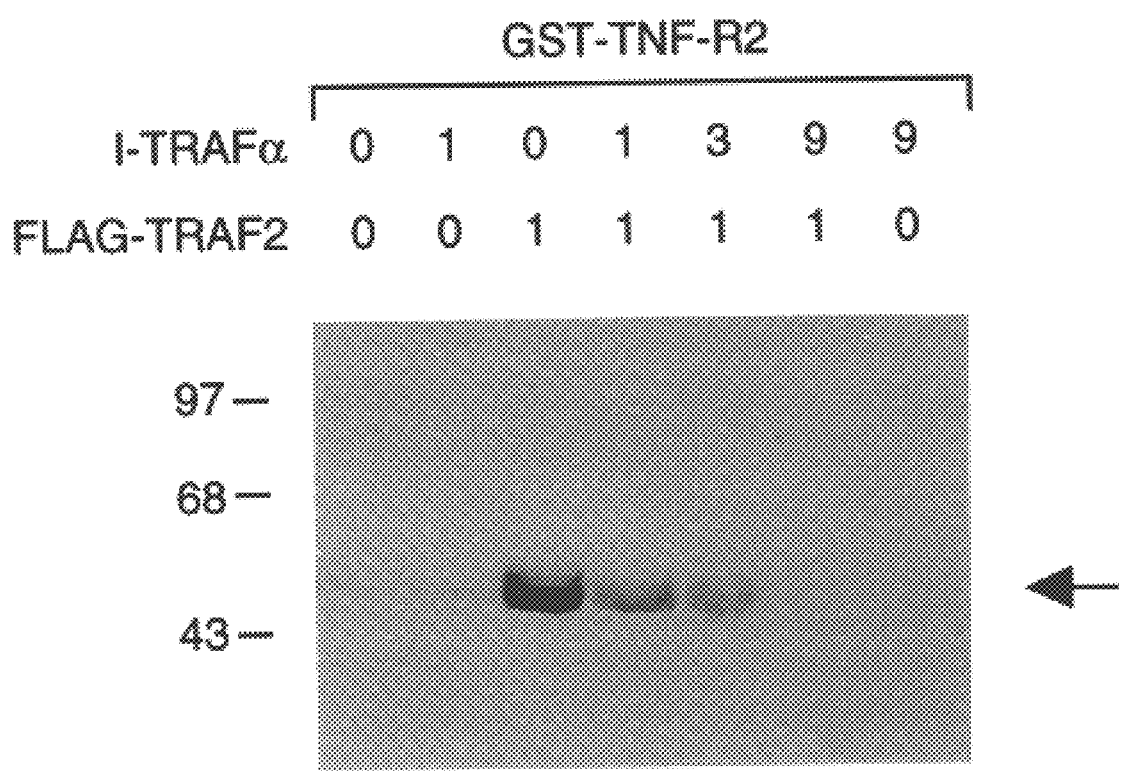
FIG. 3 shows the results of Western blot analysis which demonstrate that I-TRAF blocks the association of TRAF2 with TNF-R2.

The observed inhibitory effect of I-TRAF on the TRAF2:TNF-R2 interaction was further investigated in mammalian cells. TRAF2 and I-TRAF were expressed as full length proteins containing N-terminal FLAG epitope tags (Kodak) using the cytomegalovirus-based expression vector pRK5 (Schall et al., supra). Human embryonic kidney 293 cells (2×10$^6$) were seeded on 150 mm dishes and transfected (Ausubel et al., *Curr. Prot. Mol. Biol.* 1, 9.1.1–9.1.3 [1994]) the following day with pRK-TRAF2 (0 or 1 μg) expression vector (Rothe et al., Science in press; copending application Ser. No. 08/446,915 filed May 22, 1995) and increasing amounts of pRK-FLAG-I-TRAF (0, 1, 3, or 9 μg) expression vector. Cells were incubated at 37° C. for 24 hours, and lysed in 0.5 ml E1A buffer. 450 μl aliquots of the lysates were incubated with 10 μl GST-TNF-R2 fusion protein (Rothe et al., Cell supra; copending application Ser. No.08/446,915) bound to glutathione Sepharose beads for 15 minutes at 4° C. The beads were washed three times with 0.6 ml E1A buffer and bound proteins fractionated by 8% SDS-PAGE and transferred to a nitrocellulose membrane. Western blot analysis was performed using an anti-FLAG monoclonal antibody M2 (Kodak) and horseradishperoxidase-coupledrabbit anti-mouse immunoglobulin (Amersham). Detection was by enhanced chemiluminescenceaccording to the Amersham protocol. Western blot analysis of 50 μl aliquots of the lysates indicated that TRAF2 expression levels were similar in all samples transfected with pRK-TRAF2 (data not shown). Coexpression of TRAF2 with increasing amounts of I-TRAF effectively blocked the TRAF2:TNF-R2 interaction (FIG. 3). Furthermore, no I-TRAF was precipitatedby the TRAF2:TNF-R2 complex. These results show that TRAF2 us not able to bind TNF-R2 and I-TRAF simultaneously, possibly due to binding sites that are overlapping.

The ability of I-TRAF to bind the three known TRAF family members raised the intriguing possibility that I-TRAF functions as a general regulator of TRAF-mediated signaling events. Furthermore, the observed inhibitor effect of I-TRAF on TRAF2:TNF-R2 interaction suggested that I-TRAF expression might negatively influence TRAF2 signal transduction. Consequently, we measured the effect of I-TRAF expression on TRAF2-mediated NF-κB activation.

(5) The Inhibitory Effect of I-TRAF on Activation of NF-κB

Human embryonic kidney 293 cells were seeded at 2×10$^5$ cells/well on 6-well (35 mm) dishes and transfected (Ausubel et al., Curr. Prot. Mol. Biol. 1, 9.1.1–0.1.3 [1994]) the following day with (a) 0.5 μg pRK-TRAF2 (Rothe et al., Science in press; copending application Ser. No. 08/446, 915) (b) 1 μg pCDM8-CD40 (Rothe et al., Science supra; copending application Ser. No. 08/446,915), or (c) 0.1 μg pRK5mTNF-R2 (Lewis et al., Proc. Natl. Acad. Sci. USA 88, 2830–2834 [1991]), and increasing amounts of pRK-I-TRAF (0, 0.1, 0.32, 1.0 and 3.0 μg). Each transfection also contained 0.25 μg of pELAM-luc reported plasmid and 1 μg pRSV-βgal (Hsu et al., supra). For each of (a), (b) and (c), a control transfection containing only the pELAM-luc and pRSV-βgal was performed. After 24 hours, luciferase activities and normalizations to β-galactosidase levels were performed as described (Hsu et al., supra). Values relative to control are shown in FIG. 4 as mean ±SEM for experiments in which each transfection was performed in triplicate.

Figure 4A:
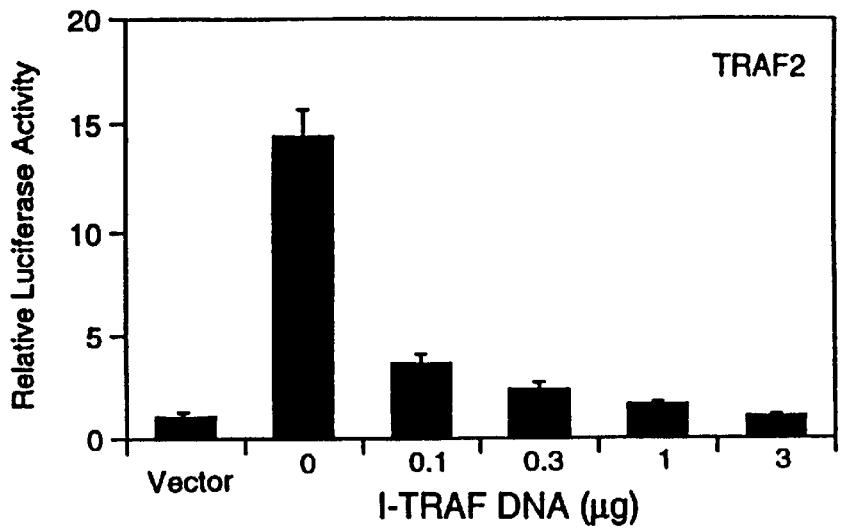
FIG. 4 illustrates the inhibitory effect of I-TRAF on activation of NF-κB.
Figure 4B:
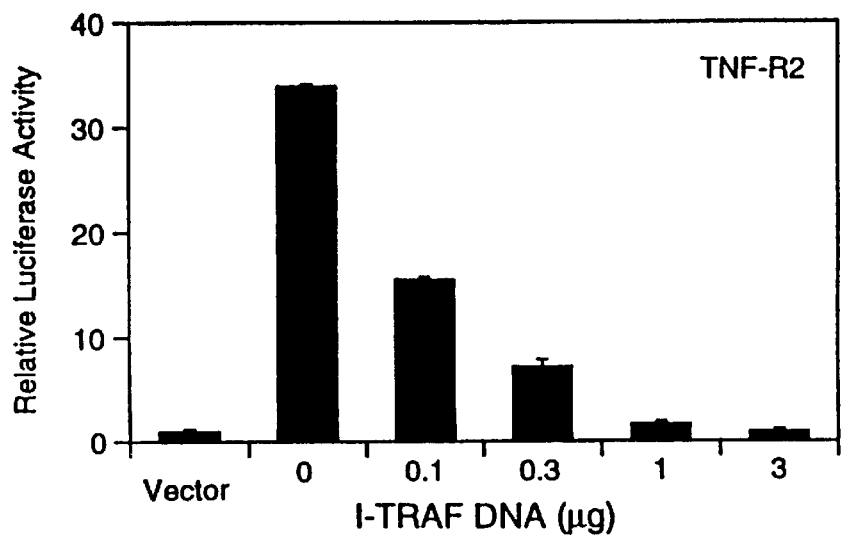
Figure 4C:
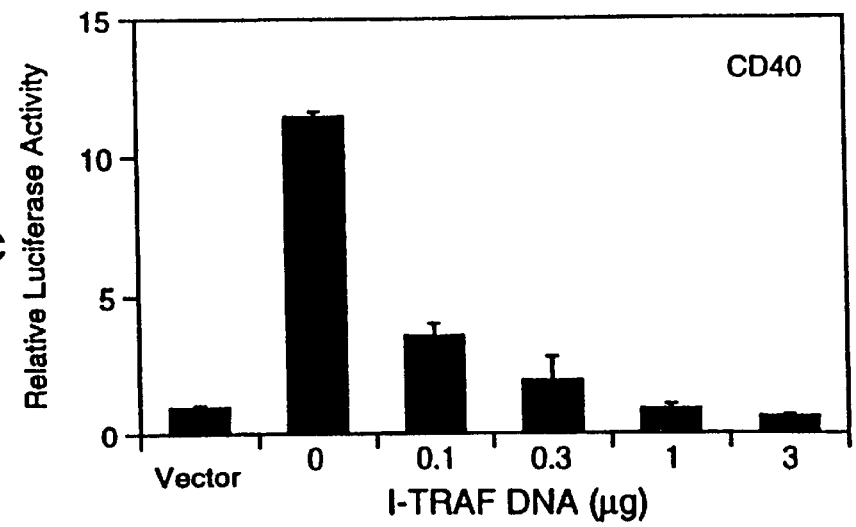

Transient expression of TRAF2 in 293 cells potently activates the NF-κB-dependent reported gene. (Rothe et al., Science supra). This activation was dramatically inhibited by I-TRAF coexpression in a dose-dependent manner (FIG. 4a). We next examined the effect of I-TRAF overexpressionon NF-κB activation triggered by the TRAF2-interactingreceptors CD40 and TNF-R2. Transient expression of these receptors has been shown to induce ligand-independent receptor aggregation which activated NF-κB in a TRAF2-dependent process. (Rothe et al., Science supra). As observed above for TRAF2, NF-κB activation through both CD40 (FIG. 4b) and TNF-R2 (FIG. 4c) was effectively blocked by increased expression of I-TRAF. NF-κB activation mediated by interleukin 1 (IL-1) was only slightly depressed by I-TRAF overexpression (data not shown). Thus, I-TRAF is a specific inhibitor of TRAF2-dependent NF-κB activation signaled by CD40 and TNF-R2.

(6) Conclusions

Conceptually, the I-TRAF/TRAF system bears remarkable similarity to the extensively studied IκB/NF-κB regulatory system (Liou and Baltimore, Curr. Op. Cell. Bio. 5, 477–487 [1993]; Thanos & Maniatis, Cell 80, 529–532 [1995]). Both systems are involved in regulating the activity of the transcription factor NF-κB through the utilization of inhibitory proteins. IκB directly regulates NF-κB function by keeping it sequestered in the cytoplasm. I-TRAF acts at an earlier step by binding to TRAFs and preventing their interaction with cell surface receptors (CD40, TNF-R2) that trigger TRAF2-mediated NF-κB activation cascades. The function of I-TRAF may be to prevent continuous TRAF signaling in the absence of ligand (CD40L or TNF). This function is consistent with the finding that TRAF2 overexpression alone, in the absence of receptor aggregation, can trigger NF-κB activation. Ligand-induced receptor aggregation might be expected to release TRAFs from I-TRAF inhibition by providing a new, higher affinity TRAF binding site.

All documents cited throughout the specification and all references cited therein are hereby expressly incorporated by reference. Although the invention has been described with reference to certain embodiments, it will be understood that certain variations and modification are possible and will be readily available for those of ordinary skill in the art. All such changes and modification and with the scope of the present invention.

We claim:

1. An isolated nucleic acid molecule capable of hybridizing under stringent conditions to the complement of SEQ ID NO: 2, with or without the nucleotide sequence of SEQ ID NO: 4 attached at the 5' end, or SEQ ID NO: 6, or SEQ ID NO: 7, or SEQ ID NO: 8, and encoding a polypeptide capable of inhibiting the interaction of a native TRAF with a cell surface receptor that triggers TRAF-mediated NF-κB activation.

2. A vector comprising and capable of expressing, in a suitable host cell, the nucleic acid molecule of claim 1.

3. A host cell transformed with the nucleic acid molecule of claim 1.

4. The isolated nucleic acid molecule of claim 1 having the sequence of SEQ ID NO: 2, with or without the nucleotide sequence of SEQ ID NO: 4 attached at the 5' end.

5. The isolated nucleic acid molecule of claim 1 having the sequence of SEQ ID NO: 6.

6. The isolated nucleic acid molecule of claim 1 having the sequence of SEQ ID NO: 7.

7. The isolated nucleic acid molecule of claim 1 having the sequence of SEQ ID NO: 8.

8. An isolated nucleic acid molecule encoding a human I-TRAF polypeptide comprising the amino acid sequence of a polypeptide selected from the group consisting of:

(a) a human I-TRAF polypeptide (SEQ ID NO:5);

(b) a murine I-TRAF-α polypeptide (SEQ ID NO:1);

(c) a murine I-TRAF-β polypeptide (SEQ ID NO:3);

(d) a truncated murine I-TRAF-α polypeptide ending with amino acids ValThrValLeuHis (VTVLH) following amino acid Gln (Q) at position 354 of the amino acid sequence shown in SEQ ID NO:1; each with or without the initiating methionine, and allelic variants thereof.

9. A vector comprising and capable of expressing, in a suitable host cell, the nucleic acid molecule of claim 8.

10. A host cell transformed with the nucleic acid molecule of claim 8.

11. A vector comprising and capable of expressing, in a suitable host cell, a nucleic acid molecule selected from the group consisting of nucleic acid molecules having the sequences of SEQ ID NO:2, with or without the nucleotide sequence of SEQ ID NO:4 attached at the 5' end, SEQ ID NO: 6, SEQ ID NO:7, and SEQ ID NO: 8.

12. A host cell transformed with any of the nucleic acid molecules of claim 11.

* * * * *